(12) United States Patent
Shortt et al.

(10) Patent No.: US 6,955,539 B2
(45) Date of Patent: Oct. 18, 2005

(54) CHARACTERIZATION OF MOTION OF DUAL MOTOR ORAL HYGIENE DEVICE

(75) Inventors: Robert A. Shortt, Laguna Niguel, CA (US); Kenneth A. Hair, Fort Collins, CO (US); Kurt M. Taylor, Fort Collins, CO (US); Danial E. Julian, Athens, IL (US)

(73) Assignee: Water Pik, Inc., Fort Collins, CO (US)

( * ) Notice: Subject to any disclaimer, the term of this patent is extended or adjusted under 35 U.S.C. 154(b) by 95 days.

(21) Appl. No.: 10/340,262

(22) Filed: Jan. 10, 2003

(65) Prior Publication Data

US 2003/0162146 A1 Aug. 28, 2003

Related U.S. Application Data

(63) Continuation-in-part of application No. 10/194,201, filed on Jul. 12, 2002.
(60) Provisional application No. 60/347,577, filed on Jan. 11, 2002, and provisional application No. 60/305,413, filed on Jul. 12, 2001.

(51) Int. Cl.$^7$ ................................................. A61C 3/03
(52) U.S. Cl. ....................................... 433/118; 132/322
(58) Field of Search ............................... 433/118, 125, 433/117, 119, 114, 166, 124, 131, 133; 132/309, 322; 15/167.1

(56) References Cited

U.S. PATENT DOCUMENTS

| | | |
|---|---|---|
| 684,951 A | 10/1901 | Rothkranz |
| 1,313,490 A | 8/1919 | Larson |
| 1,355,037 A | 10/1920 | Dziuk |
| 1,424,879 A | 8/1922 | Carlstedt |
| 1,517,320 A | 12/1924 | Stoddart |
| 1,696,835 A | 12/1928 | Burnett |
| 1,703,642 A | 2/1929 | Sticht |
| 1,796,641 A | 3/1931 | Zimmerman et al. |
| 1,832,519 A | 11/1931 | Wheat et al. |
| 1,880,617 A | 10/1932 | White |
| 2,016,597 A | 10/1935 | Drake |
| 2,044,863 A | 6/1936 | Sticht |
| 2,158,738 A | 5/1939 | Baker et al. |
| 2,206,726 A | 7/1940 | Lasater |
| 2,246,523 A | 6/1941 | Kulik |
| 2,278,365 A | 3/1942 | Daniels |
| 2,282,700 A | 5/1942 | Bobbroff |
| 2,450,635 A | 10/1948 | Dembenski |

(Continued)

FOREIGN PATENT DOCUMENTS

| | | |
|---|---|---|
| DE | 4226658 | 2/1994 |
| DE | 4241576 | 6/1994 |
| DE | 29919053 | 12/2000 |
| DE | 19961447 | 7/2001 |
| GB | 899618 | 6/2002 |
| WO | WO 98/47443 | 10/1998 |
| WO | WO 02/071970 | 9/2002 |
| WO | WO 02/071971 | 9/2002 |

*Primary Examiner*—Kevin Shaver
*Assistant Examiner*—Melba Bumgarner
(74) *Attorney, Agent, or Firm*—Dorsey & Whitney LLP

(57) ABSTRACT

An oral hygiene device is disclosed having at least two motors to simultaneously vibrate and impart motion upon the head portion of the oral hygiene device, most beneficially at the tip. A first motor is positioned in the handle portion of the device to impart a first frequency of movement to the tip. A second motor is located in a head portion, generally in a shaft of or an oral hygiene attachment to the device, to impart at least a second frequency of movement onto the tip. When both the first and second motors are activated, the resulting movement of the tip of the device may include complex, substantially random movements, depending in part on the frequencies at which the motors are operating.

32 Claims, 25 Drawing Sheets

U.S. PATENT DOCUMENTS

| | | |
|---|---|---|
| 2,577,597 A | 12/1951 | Wright et al. |
| 2,598,275 A | 5/1952 | Lakin .......................... 74/36 |
| 2,705,335 A | 4/1955 | Glassman et al. |
| 2,709,227 A | 5/1955 | Foley et al. |
| 2,728,928 A | 1/1956 | Beeren ......................... 15/29 |
| 2,734,139 A | 2/1956 | Murphy ....................... 310/29 |
| 2,806,235 A | 9/1957 | Carstairs et al. ............... 15/22 |
| 2,875,458 A | 3/1959 | Tsuda ........................... 15/22 |
| 2,917,758 A | 12/1959 | Held et al. .................... 15/22 |
| 2,931,371 A | 4/1960 | Petitta ......................... 132/89 |
| 2,962,033 A | 11/1960 | Lew |
| 2,977,614 A | 4/1961 | Demanuele .................... 15/22 |
| 3,104,405 A | 9/1963 | Perrinjaquet ................... 15/22 |
| 3,106,216 A | 10/1963 | Kirby .......................... 132/92 |
| D197,048 S | 12/1963 | Troy ............................. D9/2 |
| D197,208 S | 12/1963 | Cassidy et al. ................. D9/2 |
| 3,143,697 A | 8/1964 | Springer ....................... 320/2 |
| 3,145,404 A | 8/1964 | Fieldler ........................ 15/23 |
| D199,560 S | 11/1964 | Thompson ..................... D9/2 |
| D199,893 S | 12/1964 | Bond et al. .................... D9/2 |
| 3,159,859 A | 12/1964 | Rasmussen .................... 15/22 |
| 3,160,902 A | 12/1964 | Aymar |
| 3,168,834 A | 2/1965 | Smithson |
| 3,181,189 A | 5/1965 | Leyden ......................... 15/22 |
| 3,183,538 A | 5/1965 | Hubner ......................... 15/22 |
| D202,873 S | 11/1965 | Husted ......................... D9/2 |
| D204,127 S | 3/1966 | Syvertson ...................... D9/2 |
| 3,270,416 A | 9/1966 | Massa .......................... 32/22 |
| 3,278,963 A | 10/1966 | Bond |
| 3,289,681 A | 12/1966 | Chambers |
| 3,311,116 A | 3/1967 | Foster |
| 3,316,576 A | 5/1967 | Urbrush ........................ 15/22 |
| 3,335,443 A | 8/1967 | Parisi et al. ................... 15/22 |
| 3,346,748 A | 10/1967 | McNair ....................... 310/16 |
| 3,358,309 A | 12/1967 | Richardson .................... 15/22 |
| D210,066 S | 2/1968 | Johnson |
| 3,371,260 A | 2/1968 | Jackson et al. ................ 320/2 |
| D210,349 S | 3/1968 | Boldt |
| 3,375,820 A | 4/1968 | Kuris et al. ................... 128/62 |
| D212,208 S | 9/1968 | Rogers ......................... D4/16 |
| 3,418,552 A | 12/1968 | Holmes ........................ 320/2 |
| 3,421,524 A | 1/1969 | Waters |
| 3,430,279 A | 3/1969 | Hintze .......................... 15/23 |
| 3,463,994 A | 8/1969 | Spohr ........................... 320/2 |
| 3,466,689 A | 9/1969 | Aurelio et al. ................. 15/22 |
| 3,472,045 A | 10/1969 | Nelsen et al. .................... 64/4 |
| 3,474,799 A | 10/1969 | Borsum et al. ............... 132/91 |
| 3,535,726 A | 10/1970 | Sawyer ......................... 15/22 |
| 3,536,065 A | 10/1970 | Moret |
| 3,538,359 A | 11/1970 | Barowski ..................... 310/29 |
| 3,552,022 A | 1/1971 | Axelsson ....................... 32/58 |
| 3,559,292 A | 2/1971 | Weissman .................... 33/163 |
| 3,563,233 A | 2/1971 | Bodine ........................ 128/36 |
| 3,588,936 A | 6/1971 | Duve ........................... 15/22 |
| 3,590,814 A | 7/1971 | Bennett et al. |
| D221,823 S | 9/1971 | Cook ........................... D4/15 |
| 3,642,344 A | 2/1972 | Corker ......................... 350/6 |
| 3,651,576 A | 3/1972 | Massa ....................... 32/40 R |
| 3,660,902 A | 5/1972 | Axelsson ....................... 32/58 |
| 3,667,483 A | 6/1972 | McCabe |
| 3,672,378 A | 6/1972 | Silverman .................... 132/93 |
| 3,676,218 A | 7/1972 | Sawyer ......................... 134/1 |
| 3,759,274 A | 9/1973 | Warner ..................... 132/92 R |
| 3,760,799 A | 9/1973 | Crowson .................. 128/24 A |
| 3,809,977 A | 5/1974 | Balamuth et al. ........ 318/221 R |
| 3,831,611 A | 8/1974 | Hendricks ................. 132/92 R |
| 3,840,932 A | 10/1974 | Balamuth et al. ......... 15/167 R |
| 3,847,167 A | 11/1974 | Brien |
| D234,518 S | 3/1975 | Gerlich |
| 3,882,364 A | 5/1975 | Wright et al. ........... 318/221 R |
| 3,902,510 A | 9/1975 | Roth ......................... 132/92 A |
| 3,903,601 A | 9/1975 | Anderson et al. ............ 32/14 D |
| 3,967,617 A | 7/1976 | Krolik .......................... 128/36 |
| 3,978,852 A | 9/1976 | Annoni ..................... 128/62 A |
| 3,980,906 A | 9/1976 | Kuris et al. ................... 310/8.1 |
| 4,004,344 A | 1/1977 | Gold et al. ..................... 32/27 |
| 4,005,722 A | 2/1977 | Bragg ....................... 132/92 R |
| 4,008,728 A | 2/1977 | Sanchez ................... 132/92 R |
| 4,014,354 A | 3/1977 | Garrett |
| 4,019,522 A | 4/1977 | Elbreder ...................... 132/90 |
| 4,048,723 A | 9/1977 | Thorup ....................... 32/40 R |
| 4,064,883 A | 12/1977 | Oldham ....................... 132/93 |
| 4,133,339 A | 1/1979 | Naslund ...................... 132/89 |
| 4,141,352 A | 2/1979 | Ebner et al. |
| 4,177,434 A | 12/1979 | Ida ............................. 331/27 |
| D254,162 S | 2/1980 | Barker ......................... D4/15 |
| 4,192,035 A | 3/1980 | Kuris ........................ 15/22 R |
| 4,203,431 A | 5/1980 | Abura et al. .................. 128/39 |
| 4,205,664 A | 6/1980 | Baccialon .................. 128/62 A |
| 4,219,619 A | 8/1980 | Zarow ........................ 433/118 |
| 4,235,253 A | 11/1980 | Moore |
| 4,245,658 A | 1/1981 | Lecouturier |
| RE30,536 E | 3/1981 | Perdreaux, Jr. ............... 433/86 |
| 4,255,693 A | 3/1981 | Keidl ......................... 318/685 |
| 4,265,257 A | 5/1981 | Salyer |
| 4,271,382 A | 6/1981 | Maeda et al. ............... 318/318 |
| 4,271,384 A | 6/1981 | Beling et al. ............... 318/685 |
| 4,271,854 A | 6/1981 | Bengtsson |
| 4,275,363 A | 6/1981 | Mishiro et al. ................ 331/4 |
| 4,289,486 A | 9/1981 | Sargeant ..................... 433/118 |
| 4,307,740 A | 12/1981 | Florindez et al. ......... 132/92 R |
| 4,319,377 A | 3/1982 | Tarrson et al. ................ 15/111 |
| 4,326,547 A | 4/1982 | Verplank ...................... 132/89 |
| 4,326,548 A | 4/1982 | Wagner ....................... 132/90 |
| 4,326,549 A | 4/1982 | Hinding |
| 4,331,422 A | 5/1982 | Heyman ..................... 433/125 |
| 4,333,197 A | 6/1982 | Kuris ........................ 15/22 R |
| 4,336,622 A * | 6/1982 | Teague et al. ............... 15/22.1 |
| D265,515 S | 7/1982 | Levine ......................... D24/99 |
| 4,338,957 A | 7/1982 | Meibauer ..................... 132/91 |
| 4,347,839 A | 9/1982 | Youngclaus, Jr. .......... 138/62 A |
| 4,353,141 A | 10/1982 | Teague, Jr. et al. ......... 15/22 R |
| 4,381,478 A | 4/1983 | Saijo et al. ................. 318/135 |
| 4,395,665 A | 7/1983 | Buchas ....................... 318/114 |
| 4,397,327 A | 8/1983 | Hadary ....................... 132/89 |
| D272,565 S | 2/1984 | Levine ......................... D24/99 |
| D272,680 S | 2/1984 | Stocchi ......................... D4/25 |
| 4,429,997 A | 2/1984 | Matthews ................... 356/350 |
| 4,432,729 A | 2/1984 | Fattaleh ...................... 433/118 |
| 4,434,806 A | 3/1984 | Givens ........................ 132/91 |
| 4,442,830 A | 4/1984 | Markau ....................... 128/66 |
| 4,458,702 A | 7/1984 | Grollimund .................. 132/92 |
| 4,505,678 A | 3/1985 | Andersson ................... 433/143 |
| 4,522,355 A | 6/1985 | Moran ........................ 244/3.2 |
| 4,522,595 A | 6/1985 | Selvidge |
| 4,562,413 A | 12/1985 | Mishiro et al. ......... 331/116 R |
| 4,564,794 A | 1/1986 | Kilen et al. ................. 318/314 |
| 4,576,190 A | 3/1986 | Youssef ...................... 132/89 |
| 4,577,649 A | 3/1986 | Shimenkov .................. 132/93 |
| D283,374 S | 4/1986 | Cheuk-Yiu .................. D4/101 |
| 4,585,415 A | 4/1986 | Hommann .................... 433/80 |
| 4,586,521 A | 5/1986 | Urso |
| 4,603,448 A | 8/1986 | Middleton et al. |
| 4,605,025 A | 8/1986 | McSpadden ............... 132/92 R |
| 4,608,019 A | 8/1986 | Kumabe et al. ............. 433/118 |
| 4,617,718 A | 10/1986 | Andersson ................... 29/558 |
| 4,634,376 A | 1/1987 | Mossle et al. ................ 433/29 |
| 4,644,937 A | 2/1987 | Hommann ................... 128/66 |
| 4,655,198 A | 4/1987 | Hommann ................... 128/66 |
| 4,698,869 A | 10/1987 | Mierau et al. .............. 15/22 R |
| 4,706,695 A | 11/1987 | Urso |

| | | |
|---|---|---|
| D294,885 S | 3/1988 | Mollenhoff .................. D4/101 |
| 4,766,630 A | 8/1988 | Hegemann .................. 15/22 R |
| 4,787,847 A | 11/1988 | Martin et al. ............... 433/119 |
| 4,791,940 A | 12/1988 | Hirschfeld et al. ......... 128/776 |
| 4,811,445 A | 3/1989 | Lagieski et al. ......... 15/104.94 |
| 4,820,153 A | 4/1989 | Romhild et al. ............ 433/118 |
| 4,820,154 A | 4/1989 | Romhild et al. ............ 433/128 |
| 4,827,550 A | 5/1989 | Graham et al. ............. 15/22 R |
| 4,832,063 A | 5/1989 | Smole ........................ 132/329 |
| D301,770 S | 6/1989 | Bethany |
| 4,844,104 A | 7/1989 | Martin |
| 4,845,795 A | 7/1989 | Crawford et al. ........... 15/22 R |
| 4,856,133 A | 8/1989 | Sanchez ........................ 15/29 |
| D303,876 S | 10/1989 | Clemens et al. ............. D4/101 |
| 4,871,396 A | 10/1989 | Tsujita et al. ............ 106/286.8 |
| 4,873,496 A | 10/1989 | Ohgihara et al. ............. 331/96 |
| 4,875,265 A | 10/1989 | Yoshida |
| 4,877,934 A | 10/1989 | Spinello |
| 4,879,781 A | 11/1989 | Desimone |
| 4,880,382 A | 11/1989 | Moret et al. ................. 433/118 |
| 4,887,052 A | 12/1989 | Murakami et al. ........... 331/96 |
| 4,892,191 A | 1/1990 | Nakamura |
| 4,913,133 A | 4/1990 | Tichy ....................... 128/62 A |
| 4,913,176 A | 4/1990 | DeNiro |
| 4,922,936 A | 5/1990 | Buzzi et al. ................. 132/321 |
| D308,765 S | 6/1990 | Johnson |
| 4,974,278 A | 12/1990 | Hommann .................. 15/22 R |
| 4,989,287 A | 2/1991 | Scherer ....................... 15/22.1 |
| 4,991,249 A | 2/1991 | Suroff ......................... 15/22.2 |
| 4,995,403 A | 2/1991 | Beckman et al. ........... 128/776 |
| 5,000,684 A | 3/1991 | Odrich ....................... 433/125 |
| 5,002,487 A | 3/1991 | Tichy ......................... 433/122 |
| 5,007,127 A | 4/1991 | Paolo ............................ 15/29 |
| 5,016,660 A | 5/1991 | Boggs ........................ 132/322 |
| 5,020,179 A | 6/1991 | Scherer ....................... 15/22.1 |
| 5,033,150 A | 7/1991 | Gross et al. |
| D318,918 S | 8/1991 | Hartwein |
| D319,363 S | 8/1991 | Uemura et al. .............. D6/534 |
| 5,050,625 A | 9/1991 | Siekmann ................... 132/323 |
| D321,285 S | 11/1991 | Hirabayashi ................ D4/101 |
| 5,062,797 A | 11/1991 | Gonser |
| 5,067,223 A | 11/1991 | Bruno ....................... 29/426.5 |
| D321,986 S | 12/1991 | Snyder et al. ............... D4/101 |
| 5,068,939 A | 12/1991 | Holland ...................... 15/22.1 |
| 5,069,233 A | 12/1991 | Ritter |
| 5,069,621 A | 12/1991 | Paradis ....................... 433/147 |
| 5,071,348 A | 12/1991 | Woog ......................... 433/118 |
| 5,072,477 A | 12/1991 | Pai .............................. 15/22.1 |
| 5,077,855 A | 1/1992 | Ambasz ..................... 15/22.1 |
| 5,085,236 A | 2/1992 | Odneal et al. |
| 5,088,145 A | 2/1992 | Whitefield .................. 15/22.1 |
| 5,094,256 A | 3/1992 | Barth ......................... 132/322 |
| 5,095,470 A | 3/1992 | Oka et al. ..................... 369/13 |
| 5,100,321 A | 3/1992 | Coss et al. .................. 433/118 |
| 5,120,225 A | 6/1992 | Amit .......................... 433/216 |
| 5,123,841 A | 6/1992 | Millner ....................... 433/125 |
| 5,125,837 A | 6/1992 | Warrin et al. ................. 433/98 |
| 5,133,661 A | 7/1992 | Euvrard ...................... 433/118 |
| 5,138,733 A | 8/1992 | Bock .......................... 15/22.1 |
| 5,145,369 A | 9/1992 | Lustig et al. ................ 433/118 |
| 5,150,492 A | 9/1992 | Suroff ......................... 15/22.1 |
| 5,151,030 A | 9/1992 | Comeaux |
| 5,165,131 A | 11/1992 | Staar .......................... 15/22.1 |
| 5,169,313 A | 12/1992 | Kline ......................... 433/143 |
| 5,170,809 A | 12/1992 | Imai et al. .................. 132/322 |
| 5,174,314 A | 12/1992 | Charatan ................... 132/328 |
| 5,176,157 A | 1/1993 | Mazza |
| 5,177,826 A | 1/1993 | Vrignaud et al. ........... 15/22.1 |
| 5,180,363 A | 1/1993 | Idemoto et al. .............. 202/32 |
| 5,183,063 A | 2/1993 | Ringle et al. ............... 132/321 |
| 5,183,156 A | 2/1993 | Bruno |
| 5,184,632 A | 2/1993 | Gross et al. |
| 5,186,191 A | 2/1993 | Loubier |
| 5,188,133 A | 2/1993 | Romanus |
| 5,189,751 A | 3/1993 | Giuliani et al. .............. 15/22.1 |
| 5,193,678 A | 3/1993 | Janocik et al. |
| 5,198,732 A | 3/1993 | Morimoto ................... 318/116 |
| 5,201,092 A | 4/1993 | Colson ...................... 15/167.1 |
| 5,207,773 A | 5/1993 | Henderson |
| 5,213,434 A | 5/1993 | Hahn ........................... 403/59 |
| 5,214,819 A | 6/1993 | Kirchner ..................... 15/22.1 |
| 5,217,031 A | 6/1993 | Santoro |
| 5,224,500 A | 7/1993 | Stella ......................... 132/322 |
| 5,226,206 A | 7/1993 | Davidovitz et al. .......... 15/22.1 |
| 5,236,358 A | 8/1993 | Sieffert ....................... 433/119 |
| 5,246,022 A | 9/1993 | Israel et al. |
| 5,247,716 A | 9/1993 | Bock .......................... 15/22.1 |
| 5,253,382 A | 10/1993 | Beny ......................... 15/22.1 |
| 5,261,430 A | 11/1993 | Mochel ...................... 132/322 |
| 5,263,218 A | 11/1993 | Giuliani et al. .............. 15/22.1 |
| D341,943 S | 12/1993 | Si-Hoe ....................... D4/108 |
| 5,267,579 A | 12/1993 | Bushberger |
| D343,064 S | 1/1994 | Reno |
| 5,279,314 A | 1/1994 | Poulos et al. |
| 5,289,604 A | 3/1994 | Kressner ..................... 15/22.1 |
| 5,293,886 A | 3/1994 | Czapor ....................... 132/329 |
| 5,294,896 A | 3/1994 | Kjellander et al. ......... 331/158 |
| D346,212 S | 4/1994 | Hosl |
| 5,299,723 A | 4/1994 | Hempel |
| 5,305,492 A | 4/1994 | Giuliani et al. ............ 15/176.1 |
| 5,309,590 A | 5/1994 | Giuliani et al. .............. 15/22.1 |
| 5,311,632 A | 5/1994 | Center ........................ 15/22.1 |
| 5,311,633 A | 5/1994 | Herzog et al. ................. 15/28 |
| 5,323,796 A | 5/1994 | Herzog et al. .............. 132/322 |
| 5,337,435 A | 8/1994 | Krasner et al. ................. 15/23 |
| 5,341,534 A | 8/1994 | Serbinski et al. ............ 15/22.1 |
| 5,353,460 A | 10/1994 | Bauman ..................... 15/22.1 |
| 5,354,246 A | 10/1994 | Gotman ..................... 475/248 |
| 5,355,638 A | 10/1994 | Hoffman ..................... 451/32 |
| 5,358,328 A | 10/1994 | Inoue et al. ................... 366/65 |
| 5,359,747 A | 11/1994 | Amakasu .................... 15/22.1 |
| D353,490 S | 12/1994 | Hartwein .................... D4/108 |
| 5,369,831 A | 12/1994 | Bock .......................... 15/22.1 |
| D354,168 S | 1/1995 | Hartwein .................... D4/108 |
| 5,378,153 A | 1/1995 | Giuliani et al. ............. 433/216 |
| 5,383,242 A | 1/1995 | Bigler et al. ................. 15/22.1 |
| 5,393,229 A | 2/1995 | Ram .......................... 433/118 |
| 5,400,811 A | 3/1995 | Meibauer |
| 5,404,608 A | 4/1995 | Hommann .................. 15/22.1 |
| 5,406,664 A | 4/1995 | Hukuba ...................... 15/22.1 |
| D358,486 S | 5/1995 | Loew ......................... D4/104 |
| 5,358,713 S | 5/1995 | Perry ......................... D4/104 |
| D358,801 S | 5/1995 | Vos ........................... D13/108 |
| 5,411,041 A | 5/1995 | Ritter ......................... 132/322 |
| 5,412,827 A | 5/1995 | Muller et al. ................ 15/22.1 |
| 5,416,942 A | 5/1995 | Baldacci et al. ............. 15/22.1 |
| 5,419,346 A | 5/1995 | Tipp .......................... 132/329 |
| 5,419,703 A | 5/1995 | Warrin et al. ............... 433/216 |
| 5,421,726 A | 6/1995 | Okada ....................... 433/216 |
| D363,605 S | 10/1995 | Kou et al. ................... D4/101 |
| 5,459,898 A | 10/1995 | Bacolot ........................ 15/106 |
| 5,467,494 A | 11/1995 | Muller et al. ................ 15/22.1 |
| 5,467,495 A | 11/1995 | Boland et al. ................. 15/28 |
| 5,482,466 A | 1/1996 | Haynes ...................... 132/323 |
| 5,484,281 A | 1/1996 | Renow et al. ................. 433/80 |
| 5,496,256 A | 3/1996 | Bock et al. ..................... 601/2 |
| 5,499,420 A | 3/1996 | Boland |
| 5,504,958 A | 4/1996 | Herzog ....................... 15/22.1 |
| 5,511,270 A | 4/1996 | Eliachar et al. ............. 15/22.1 |
| 5,511,275 A | 4/1996 | Volpenhein et al. ....... 15/167.1 |
| D370,125 S | 5/1996 | Craft et al. .................. D4/101 |
| D370,347 S | 6/1996 | Heinzelman et al. ........ D4/104 |

| Patent No. | Date | Name |
|---|---|---|
| 5,529,494 A | 6/1996 | Vlacancich ............ 433/105 |
| D371,242 S | 7/1996 | Shimatsu et al. ......... D4/108 |
| 5,545,968 A | 8/1996 | Hilfinger et al. |
| 5,546,624 A | 8/1996 | Bock .................. 15/22.1 |
| D375,841 S | 11/1996 | Serbinski .............. D4/108 |
| 5,573,020 A | 11/1996 | Robinson ............... 132/322 |
| 5,577,285 A | 11/1996 | Drossler ............... 15/22.1 |
| 5,579,786 A | 12/1996 | Wolk et al. ............ 132/322 |
| 5,588,452 A | 12/1996 | Peck |
| 5,606,984 A | 3/1997 | Gao .................... 132/325 |
| 5,613,258 A | 3/1997 | Hilfinger et al. ....... 15/22.1 |
| 5,617,601 A | 4/1997 | McDougall .............. 15/22.1 |
| 5,618,275 A | 4/1997 | Bock ................... 604/290 |
| 5,619,766 A | 4/1997 | Zhadanov et al. ........ 15/29 |
| 5,625,916 A | 5/1997 | McDougall .............. 15/28 |
| D381,468 S | 7/1997 | Dolan et al. |
| 5,651,157 A | 7/1997 | Hahn ................... 15/22.1 |
| D382,407 S | 8/1997 | Craft et al. ........... D4/101 |
| 5,652,990 A | 8/1997 | Driesen et al. ......... 15/28 |
| 5,678,274 A | 10/1997 | Liu .................... 15/167.1 |
| 5,678,578 A | 10/1997 | Kossak et al. |
| 5,697,117 A | 12/1997 | Craft .................. 15/22.1 |
| 5,700,146 A | 12/1997 | Kucar .................. 433/82 |
| RE35,712 E | 1/1998 | Murayama |
| 5,709,233 A | 1/1998 | Boland et al. .......... 132/322 |
| 5,718,667 A | 2/1998 | Sugimoto et al. ........ 601/139 |
| 5,732,433 A | 3/1998 | Göcking et al. ......... 15/28 |
| 5,738,575 A | 4/1998 | Bock ................... 433/216 |
| 5,749,380 A | 5/1998 | Zebuhr |
| 5,762,078 A | 6/1998 | Zebuhr |
| 5,775,346 A | 7/1998 | Szyszkowski |
| 5,784,742 A | 7/1998 | Giuliani et al. |
| 5,816,271 A | 10/1998 | Urso |
| D400,713 S | 11/1998 | Solanki ................ D4/104 |
| D403,511 S | 1/1999 | Serbinski .............. D4/108 |
| 5,893,175 A | 4/1999 | Cooper |
| 5,901,397 A | 5/1999 | Hafele et al. |
| D410,787 S | 6/1999 | Barre et al. ........... D4/104 |
| D411,769 S | 7/1999 | Wright |
| 5,921,254 A | 7/1999 | Carlucci et al. |
| 5,927,976 A | 7/1999 | Wu |
| 5,934,908 A | 8/1999 | Woog et al. |
| D413,694 S | 9/1999 | Bennett |
| D414,937 S | 10/1999 | Cornu et al. ........... D4/104 |
| D414,939 S | 10/1999 | Pedro, Jr. et al. ...... D4/104 |
| D417,960 S | 12/1999 | Moskovich et al. ....... D4/104 |
| 6,026,828 A | 2/2000 | Altshuler |
| 6,047,711 A | 4/2000 | Wagner |
| 6,050,818 A | 4/2000 | Boland et al. |
| RE36,699 E | 5/2000 | Murayama |
| D423,784 S | 5/2000 | Joulin ................. D4/104 |
| 6,092,252 A | 7/2000 | Fischer et al. |
| 6,102,700 A | 8/2000 | Haczek et al. |
| 6,106,294 A | 8/2000 | Daniel |
| 6,138,310 A | 10/2000 | Porper et al. |
| 6,140,723 A | 10/2000 | Matsui et al. |
| 6,148,462 A | 11/2000 | Zseng |
| 6,154,912 A | 12/2000 | Li |
| D437,090 S | 1/2001 | Lang et al. |
| D437,091 S | 1/2001 | Lang et al. |
| 6,178,579 B1 | 1/2001 | Blaustein et al. |
| D437,663 S | 2/2001 | Lang et al. |
| D437,976 S | 2/2001 | Narayanan et al. |
| D437,977 S | 2/2001 | Lang et al. |
| D438,306 S | 2/2001 | Narayanan |
| 6,195,828 B1 | 3/2001 | Fritsch |
| 6,202,242 B1 | 3/2001 | Salmon et al. |
| 6,203,320 B1 | 3/2001 | Williams et al. |
| 6,220,857 B1 | 4/2001 | Abels |
| 6,230,354 B1 | 5/2001 | Sproat |
| 6,230,717 B1 | 5/2001 | Marx et al. |
| 6,237,178 B1 | 5/2001 | Krammer et al. |
| 6,253,404 B1 | 7/2001 | Boland et al. |
| 6,267,593 B1 | 7/2001 | Haczek et al. |
| 6,308,358 B2 | 10/2001 | Gruber et al. |
| 6,308,359 B2 | 10/2001 | Fritsch et al. |
| 6,341,400 B1 | 1/2002 | Kobayashi et al. |
| 6,343,396 B1 | 2/2002 | Simovitz et al. |
| 6,343,400 B1 | 2/2002 | Massholder et al. |
| 6,347,425 B1 | 2/2002 | Fattori et al. |
| 6,353,956 B1 | 3/2002 | Berge |
| 6,360,395 B2 | 3/2002 | Blaustein et al. |
| 6,363,565 B1 | 4/2002 | Paffrath |
| 6,367,108 B1 | 4/2002 | Fritsch et al. |
| 6,374,448 B2 | 4/2002 | Seifert |
| 6,381,795 B1 | 5/2002 | Hofmann et al. |
| 6,401,288 B1 | 6/2002 | Porper et al. |
| 6,421,865 B1 | 7/2002 | McDougall |
| 6,421,866 B1 | 7/2002 | McDougall |
| 6,421,867 B1 | 7/2002 | Weihrauch |
| 6,422,867 B2 | 7/2002 | Lang et al. |
| 6,434,773 B1 | 8/2002 | Kuo |
| D463,627 S | 9/2002 | Lang et al. |
| 6,446,294 B1 | 9/2002 | Specht |
| 6,446,295 B1 | 9/2002 | Calabrese |
| 6,447,293 B1 | 9/2002 | Sokol et al. |
| 6,453,497 B1 | 9/2002 | Chiang et al. |
| 6,453,498 B1 | 9/2002 | Wu |
| 6,453,499 B1 | 9/2002 | Leuermann |
| 6,463,615 B1 | 10/2002 | Gruber et al. |
| 6,490,747 B1 | 12/2002 | Metwally |
| 6,497,237 B1 | 12/2002 | Ali |
| 6,510,575 B2 | 1/2003 | Calabrese |
| 6,526,994 B1 | 3/2003 | Santoro |
| 6,536,066 B2 | 3/2003 | Dickie |
| 6,564,940 B2 | 5/2003 | Blaustein et al. |
| 6,571,804 B2 | 6/2003 | Adler |
| 6,574,820 B1 | 6/2003 | DePuydt et al. |
| 6,581,233 B1 | 6/2003 | Cheng |
| 6,581,234 B2 | 6/2003 | Lee et al. |
| 6,588,042 B2 | 7/2003 | Fritsch et al. |
| 6,599,048 B2 | 7/2003 | Kuo |
| 6,609,910 B2 | 8/2003 | Narayanan |
| 6,622,333 B1 | 9/2003 | Rehkemper et al. |
| 6,647,577 B2 | 11/2003 | Tam |
| D484,311 S | 12/2003 | Cacka et al. |
| 6,654,979 B2 | 12/2003 | Calabrese |
| 6,665,901 B2 | 12/2003 | Driesen et al. |
| 6,691,363 B2 | 2/2004 | Huen |
| 6,701,565 B2 | 3/2004 | Hafemann |
| 6,721,986 B2 | 4/2004 | Zhuan |
| 6,725,490 B2 | 4/2004 | Blaustein et al. |
| 6,735,803 B2 | 5/2004 | Kuo |
| 6,735,804 B2 | 5/2004 | Carlucci et al. |
| 6,739,012 B2 | 5/2004 | Grez et al. |
| 6,751,823 B2 | 6/2004 | Biro et al. |
| 6,760,945 B2 | 7/2004 | Ferber et al. |
| 6,760,946 B2 | 7/2004 | DePuydt |
| 6,766,548 B1 | 7/2004 | Lukas et al. |
| 6,766,549 B2 | 7/2004 | Klupt |
| 6,779,126 B1 | 8/2004 | Lin et al. |
| 6,779,215 B2 | 8/2004 | Hartman et al. |
| 6,785,926 B2 | 9/2004 | Green |
| 6,792,640 B2 | 9/2004 | Lev |
| 6,795,993 B2 | 9/2004 | Lin |
| 6,798,169 B2 | 9/2004 | Stratmann et al. |
| 6,799,346 B2 | 10/2004 | Jeng et al. |
| 6,802,097 B2 | 10/2004 | Hafliger et al. |
| 6,813,793 B2 | 11/2004 | Eliav |
| 6,813,794 B2 | 11/2004 | Weng |
| 6,821,119 B2 | 11/2004 | Shortt et al. |
| 6,823,875 B2 | 11/2004 | Hotta et al. |

| | | |
|---|---|---|
| 2001/0016963 A1 | 8/2001 | Driesen et al. |
| 2001/0039955 A1 | 11/2001 | Winters et al. |
| 2002/0017474 A1 | 2/2002 | Blaustein et al. |
| 2002/0029988 A1 | 3/2002 | Blaustein et al. |
| 2002/0039720 A1 | 4/2002 | Marx et al. |
| 2002/0059685 A1 | 5/2002 | Paffrath |
| 2002/0066147 A1 | 6/2002 | Schutz |
| 2002/0078514 A1 | 6/2002 | Blaustein et al. |
| 2002/0084707 A1 | 7/2002 | Tang |
| 2002/0088068 A1 | 7/2002 | Levy et al. |
| 2002/0095734 A1 | 7/2002 | Wong |
| 2002/0100134 A1 | 8/2002 | Dunn et al. |
| 2002/0106607 A1 | 8/2002 | Horowitz |
| 2002/0108193 A1 | 8/2002 | Gruber |
| 2002/0116775 A1 | 8/2002 | Wong |
| 2002/0120991 A1 | 9/2002 | Cacka et al. |
| 2002/0121283 A1 | 9/2002 | Piccolo et al. |
| 2002/0129454 A1 | 9/2002 | Hilscher et al. |
| 2002/0138926 A1 | 10/2002 | Brown, Jr. et al. |
| 2002/0152563 A1 | 10/2002 | Sato |
| 2002/0152564 A1 | 10/2002 | Blaustein et al. |
| 2002/0162180 A1 | 11/2002 | Blaustein et al. |
| 2002/0166188 A1 | 11/2002 | Driesen et al. |
| 2002/0170570 A1 | 11/2002 | Bergman |
| 2002/0174498 A1 | 11/2002 | Li |
| 2002/0178519 A1 | 12/2002 | Zarlengo |
| 2002/0184719 A1 | 12/2002 | Eliav et al. |
| 2002/0185149 A1 | 12/2002 | Ali |
| 2003/0005544 A1 | 1/2003 | Felix |
| 2003/0029472 A1 | 2/2003 | Adler |
| 2003/0033679 A1 | 2/2003 | Fattori et al. |
| 2003/0033680 A1 | 2/2003 | Davies et al. |
| 2003/0041396 A1 | 3/2003 | Dickie |
| 2003/0041397 A1 | 3/2003 | Hafemann |
| 2003/0064348 A1 | 4/2003 | Sokol et al. |
| 2003/0066145 A1 | 4/2003 | Prineppi |
| 2003/0074751 A1 | 4/2003 | Wu |
| 2003/0079305 A1 | 5/2003 | Takahata et al. |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0084528 A1 | 5/2003 | Chan et al. |
| 2003/0097723 A1 | 5/2003 | Li |
| 2003/0098037 A1 | 5/2003 | Dougan et al. |
| 2003/0101526 A1 | 6/2003 | Hilscher et al. |
| 2003/0106175 A1 | 6/2003 | Lam |
| 2003/0106565 A1 | 6/2003 | Andrews |
| 2003/0111091 A1 | 6/2003 | Hotta et al. |
| 2003/0126699 A1 | 7/2003 | Blaustein et al. |
| 2003/0131427 A1 | 7/2003 | Hilscher et al. |
| 2003/0140435 A1 | 7/2003 | Eliav et al. |
| 2003/0140436 A1 | 7/2003 | Gatzemeyer et al. |
| 2003/0140437 A1 | 7/2003 | Eliav et al. |
| 2003/0140937 A1 | 7/2003 | Cook |
| 2003/0140939 A1 | 7/2003 | Nudo, Sr. |
| 2003/0150474 A1 | 8/2003 | Doyscher |
| 2003/0154567 A1 | 8/2003 | Drossler et al. |
| 2003/0154568 A1 | 8/2003 | Boland et al. |
| 2003/0163881 A1 | 9/2003 | Driesen et al. |
| 2003/0163882 A1 | 9/2003 | Blaustein et al. |
| 2003/0182743 A1 | 10/2003 | Gatzemeyer et al. |
| 2003/0182744 A1 | 10/2003 | Fattori et al. |
| 2003/0182746 A1 | 10/2003 | Fattori et al. |
| 2003/0192139 A1 | 10/2003 | Fattori et al. |
| 2003/0196283 A1 | 10/2003 | Eliav et al. |
| 2003/0196677 A1 | 10/2003 | Wiseman |
| 2003/0204925 A1 | 11/2003 | Hall et al. |
| 2003/0213075 A1 | 11/2003 | Hui et al. |
| 2003/0213076 A1 | 11/2003 | Schutz et al. |
| 2003/0221267 A1 | 12/2003 | Chan |
| 2003/0221269 A1 | 12/2003 | Zhuan |
| 2003/0226223 A1 | 12/2003 | Chan |
| 2004/0010869 A1 | 1/2004 | Fattori et al. |
| 2004/0010870 A1 | 1/2004 | McNair |
| 2004/0010871 A1 | 1/2004 | Nishinaka et al. |
| 2004/0010872 A1 | 1/2004 | Chiang |
| 2004/0016067 A1 | 1/2004 | Kraemer |
| 2004/0016068 A1 | 1/2004 | Lee |
| 2004/0016069 A1 | 1/2004 | Lee |
| 2004/0019987 A1 | 2/2004 | Chu |
| 2004/0025274 A1 | 2/2004 | Moskovich et al. |
| 2004/0034951 A1 | 2/2004 | Davies et al. |
| 2004/0045106 A1 | 3/2004 | Lam |
| 2004/0045107 A1 | 3/2004 | Egeresi |
| 2004/0049867 A1 | 3/2004 | Hui |
| 2004/0049868 A1 | 3/2004 | Ng |
| 2004/0060132 A1 | 4/2004 | Gatzemeyer et al. |
| 2004/0060134 A1 | 4/2004 | Eliav et al. |
| 2004/0060135 A1 | 4/2004 | Gatzemeyer et al. |
| 2004/0060136 A1 | 4/2004 | Gatzemeyer et al. |
| 2004/0060137 A1 | 4/2004 | Eliav |
| 2004/0068811 A1 | 4/2004 | Fulop et al. |
| 2004/0074026 A1 | 4/2004 | Blaustein et al. |
| 2004/0083566 A1 | 5/2004 | Blaustein et al. |
| 2004/0087882 A1 | 5/2004 | Roberts et al. |
| 2004/0088806 A1 | 5/2004 | DePuydt et al. |
| 2004/0088807 A1 | 5/2004 | Blaustein et al. |
| 2004/0091834 A1 | 5/2004 | Rizoiu et al. |
| 2004/0107521 A1 | 6/2004 | Chan et al. |
| 2004/0123409 A1 | 7/2004 | Dickie |
| 2004/0128777 A1 | 7/2004 | Koh |
| 2004/0128778 A1 | 7/2004 | Wong |
| 2004/0128779 A1 | 7/2004 | Chan et al. |
| 2004/0128780 A1 | 7/2004 | Chan |
| 2004/0134001 A1 | 7/2004 | Chan |
| 2004/0143917 A1 | 7/2004 | Ek |
| 2004/0154112 A1 | 8/2004 | Braun et al. |
| 2004/0154113 A1 | 8/2004 | Drossler et al. |
| 2004/0158944 A1 | 8/2004 | Fattori |
| 2004/0163191 A1 | 8/2004 | Cuffaro et al. |
| 2004/0168269 A1 | 9/2004 | Kunita et al. |
| 2004/0168270 A1 | 9/2004 | Choi et al. |
| 2004/0168271 A1 | 9/2004 | McDougall |
| 2004/0168272 A1 | 9/2004 | Prineppi |
| 2004/0177458 A1 | 9/2004 | Chan et al. |
| 2004/0187889 A1 | 9/2004 | Kemp et al. |
| 2004/0200016 A1 | 10/2004 | Chan et al. |
| 2004/0202981 A1 | 10/2004 | Luettgen et al. |

* cited by examiner

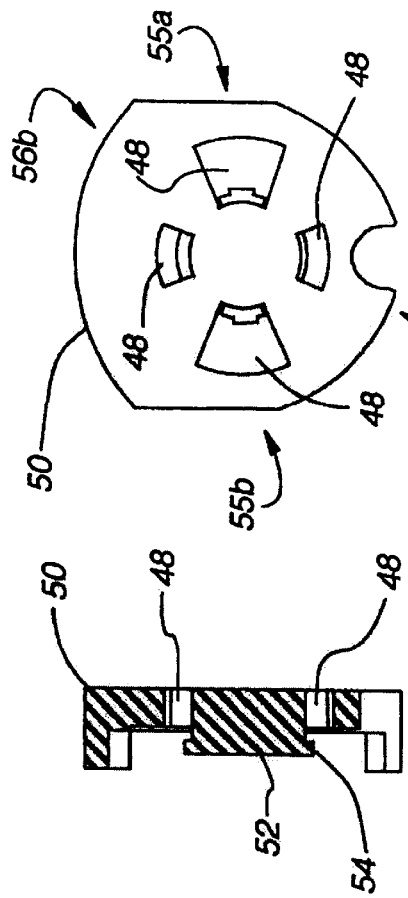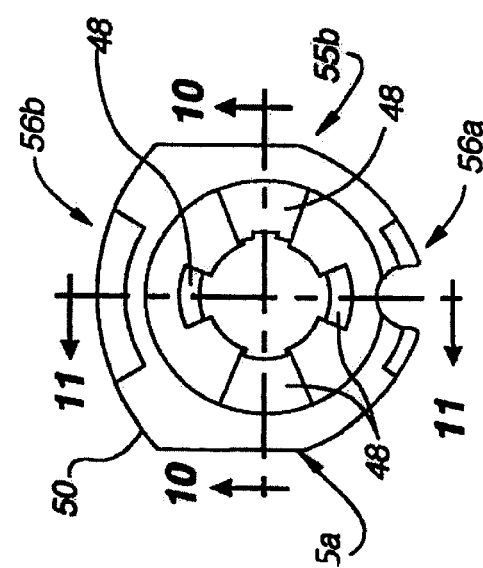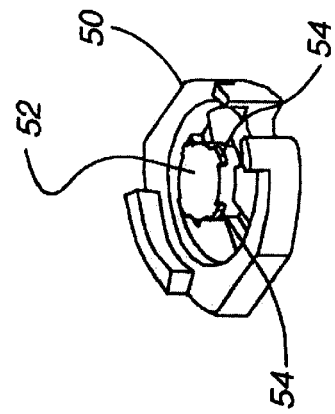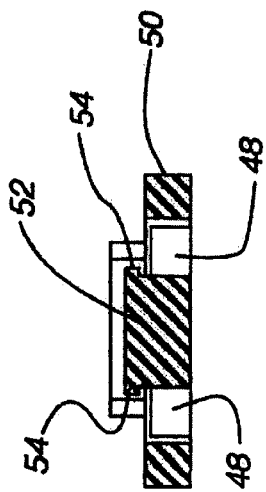

EXAMPLE OF BRISTLE MOTION: SECONDARY MOTOR OPERATING

EXAMPLE OF BRISTLE MOTION: PRIMARY MOTOR OPERATING
& SECONDARY MOTOR OPERATING

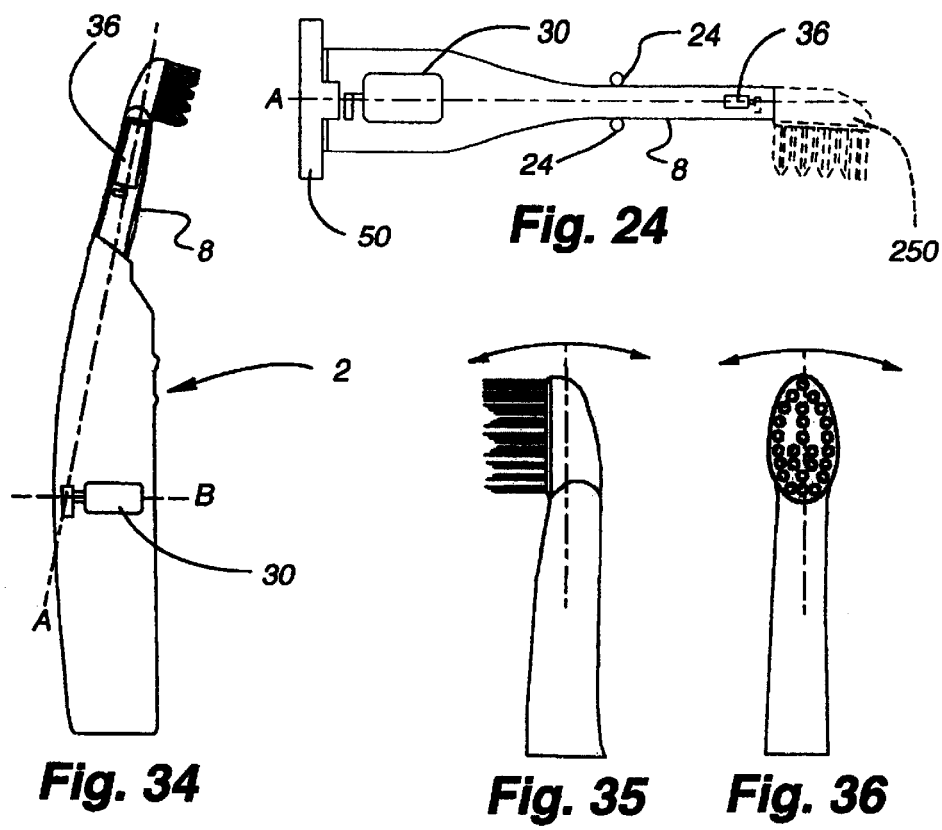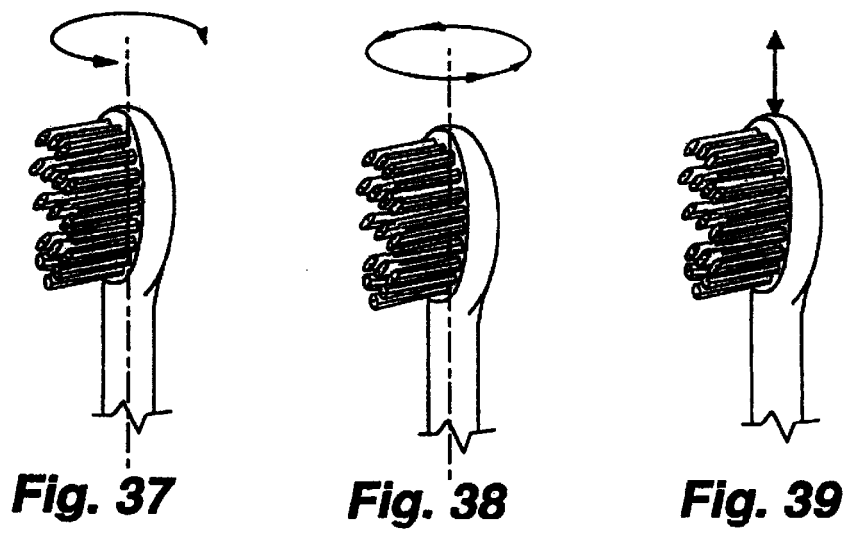

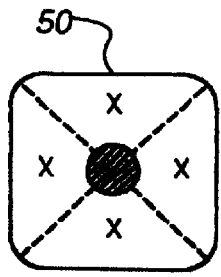 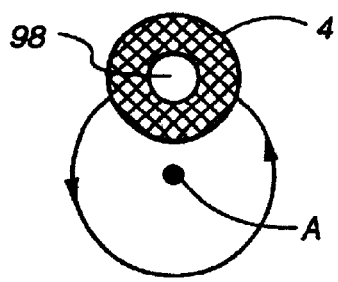 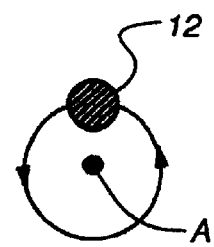
*Fig. 25A*   *Fig. 25B*   *Fig. 25C*
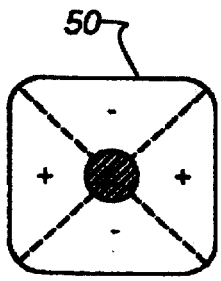 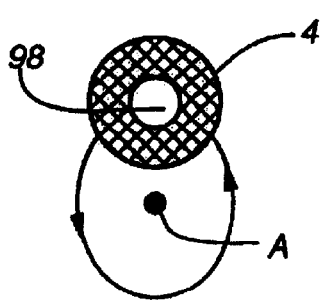 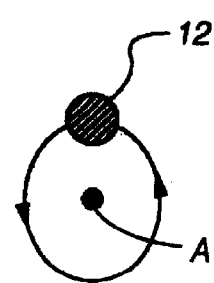
*Fig. 26A*   *Fig. 26B*   *Fig. 26C*
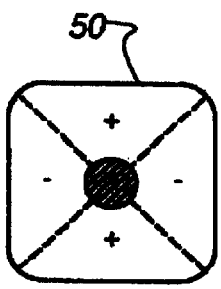 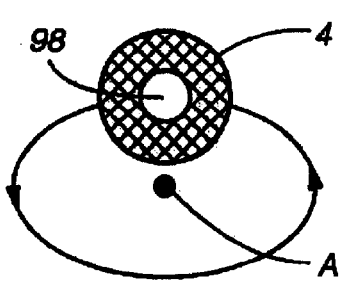 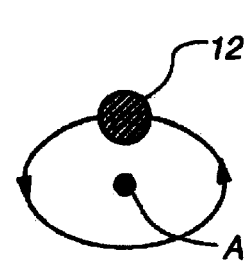
*Fig. 27A*   *Fig. 27B*   *Fig. 27C*
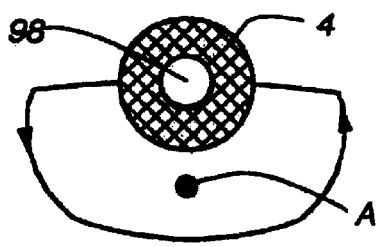 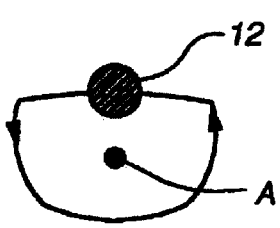
*Fig. 28A*   *Fig. 28B*

| TIME | PIXEL X | PIXEL Y | mm X | mm Y |
|---|---|---|---|---|
| 0 | 13 | 7 | 1.04 | 0.56 |
| 0.0005 | 15 | 5 | 1.20 | 0.40 |
| 0.001 | 18 | 4 | 1.44 | 0.32 |
| 0.0015 | 19 | 4 | 1.52 | 0.32 |
| 0.002 | 18 | 4 | 1.44 | 0.32 |
| 0.0025 | 15 | 5 | 1.20 | 0.40 |
| 0.003 | 13 | 6 | 1.04 | 0.48 |
| 0.0035 | 12 | 6 | 0.96 | 0.48 |
| 0.004 | 11 | 6 | 0.88 | 0.48 |
| 0.0045 | 9 | 4 | 0.72 | 0.32 |
| 0.005 | 7 | 3 | 0.56 | 0.24 |
| 0.0055 | 4 | 2 | 0.32 | 0.16 |
| 0.006 | 2 | 2 | 0.16 | 0.16 |
| 0.0065 | 1 | 4 | 0.08 | 0.32 |
| 0.007 | 3 | 6 | 0.24 | 0.48 |
| 0.0075 | 7 | 8 | 0.56 | 0.64 |
| 0.008 | 11 | 8 | 0.88 | 0.64 |
| 0.0085 | 15 | 7 | 1.20 | 0.56 |

SHAFT
(NO BRUSH HEAD END)

SHAFT MOTION
(WITHOUT BRUSH HEAD)
(BRISTLES POINT UP)

| TIME | PIXEL X | PIXEL Y | mm X | mm Y |
|---|---|---|---|---|
| 0 | 25 | 44 | 0.89 | 0.83 |
| 0.0005 | 27 | 43 | 1.05 | 0.76 |
| 0.001 | 27 | 41 | 1.05 | 0.61 |
| 0.0015 | 28 | 40 | 1.12 | 0.53 |
| 0.002 | 27 | 38 | 1.05 | 0.38 |
| 0.0025 | 26 | 36 | 0.97 | 0.23 |
| 0.003 | 25 | 36 | 0.89 | 0.23 |
| 0.0035 | 23 | 36 | 0.74 | 0.23 |
| 0.004 | 20 | 36 | 0.52 | 0.23 |
| 0.0045 | 19 | 38 | 0.44 | 0.38 |
| 0.005 | 18 | 41 | 0.36 | 0.61 |
| 0.0055 | 18 | 43 | 0.36 | 0.76 |
| 0.006 | 20 | 45 | 0.52 | 0.91 |
| 0.0065 | 22 | 46 | 0.67 | 0.98 |
| 0.007 | 24 | 45 | 0.82 | 0.91 |
| 0.0075 | 27 | 43 | 1.05 | 0.76 |

BRUSH HEAD END

BRUSH HEAD MOTION
(BRISTLES POINT UP)

| TIME | PIXEL X | PIXEL Y | mm X | mm Y |
|---|---|---|---|---|
| 0 | 42 | 73 | 1.18 | 0.53 |
| 0.0005 | 42 | 73 | 1.18 | 0.45 |
| 0.001 | 41 | 71 | 1.11 | 0.38 |
| 0.015 | 41 | 70 | 1.11 | 0.30 |
| 0.002 | 39 | 69 | 0.95 | 0.23 |
| 0.0025 | 34 | 71 | 0.58 | 0.38 |
| 0.003 | 31 | 73 | 0.35 | 0.53 |
| 0.0035 | 30 | 74 | 0.27 | 0.61 |
| 0.004 | 32 | 76 | 0.42 | 0.76 |
| 0.0045 | 36 | 76 | 0.73 | 0.76 |
| 0.005 | 40 | 77 | 1.03 | 0.83 |
| 0.0055 | 42 | 76 | 1.18 | 0.76 |
| 0.006 | 42 | 73 | 1.18 | 0.53 |

INDIVIDUAL BRISTLE END

BRISTLE MOTION
(BRISTLES POINT UP)

CHARACTERIZATION OF MOTION OF DUAL MOTOR ORAL HYGIENE DEVICE

CROSS REFERENCE TO RELATED APPLICATIONS

This application is a continuation-in-part of U.S. application Ser. No. 10/194,201 filed Jul. 12, 2002, the disclosure of which is hereby incorporated herein by reference in its entirety. This application also claims priority to commonly owned U.S. provisional application No. 60/347,577, filed Jan. 11, 2002, the disclosure of which is hereby incorporated herein by reference in its entirety. This application is also related to U.S. provisional application No. 60/305,413, filed Jul. 12, 2001, the disclosure of which is hereby incorporated herein by reference in its entirety.

BACKGROUND OF THE INVENTION

1. Field of the Invention

This invention relates to a powered oral hygiene device having at least two motors to vibrate the device head and the resultant motions of the brush head.

2. Description of Related Art

Typically, electric oral hygiene devices such as electric toothbrushes include a single motor which drives a motion-creating mechanism, which in turn causes the head of the device to move during use. Such motion, commonly in the form of linear reciprocation, rotation or oscillation, enhances the cleaning of one's teeth. Because a typical electric toothbrush includes only a single motor, the automatic motions of the electric toothbrush are generally limited.

As recognized by the present inventors, there is a need for an oral hygiene device having complex vibrations or movements at the head of the oral hygiene device to provide a useful cleaning or polishing effect for teeth.

It is against this background that various embodiments of the present invention were developed. The features, utilities and advantages of the various embodiments of the invention will be apparent from the following more particular description of embodiments of the invention as illustrated in the accompanying drawings.

SUMMARY OF THE INVENTION

Disclosed herein are various embodiments of an oral hygiene device, each having at least two motors to simultaneously vibrate or impart motion upon the head portion of the oral hygiene device, most beneficially at the tip. In one embodiment, a first motor is positioned in the handle portion of the oral hygiene device to impart a first frequency of movement to the tip of the oral hygiene device, and a second motor is located in a head portion, generally in a shaft or an oral hygiene attachment to the oral hygiene device, to impart at least a second frequency of movement onto the tip of the device. When both the first and second motors are activated, the resulting movement of the tip of the oral hygiene device may include complex, substantially random movements, depending in part on the frequencies at which the motors are operating. In one embodiment described herein off-center or "eccentric" mass motors mounted at different locations in the handle portion and head portion are used to create vibrational movement of the tip, with the specific movement of the tip being substantially random or chaotic.

As used herein, the term "movement" encompasses the movement of the shaft of an oral hygiene device that accepts oral hygiene attachments, the tip of a single member, for example, a flosser tip, or the tip of a bristle in a group of bristles, or the tips of a group of bristles as a whole, or the operating end of any other oral hygiene attachment. It can also relate to the movement of the base portion of the particular tip attached to the device, such as the base of the flosser tip, which may move differently than the tip of the flosser due to the physical characteristics of the flosser itself (e.g., length, shape, material, and flexing characteristics). The types of movement contemplated by the present invention may include: translational (e.g., as a wiper blade on a car windshield); rotational (about a longitudinal axis, e.g., the motion of a drill bit, either continuously clockwise or counterclockwise or alternating clockwise and counterclockwise); oscillatory (back and forth along the same path); pivotal (about a single pivot point, or other structure allowing pivotal movement in many planes); and orbital motion (such as a tip translating around a center point to form a closed loop path), or any combination thereof. These types of movements may be reciprocating (back and forth, in and out, up and down), oscillating, or any type of generally vibrating characteristic. The terms "vibration," "vibratory," or "vibrational" as used herein are meant to encompass any of the movements effected upon the oral hygiene device described above.

The movement of the head portion can take place in a single plane or in multiple planes. The movement of the various oral hygiene attachments used with the inventive oral hygiene device can be controlled, for example, by the position, orientation, and type of drive motor(s), associated drive linkage, the interaction between the motors and the housing, positioning structures, and dampening structures. A vibration focusing structure, for example, a rubber or elastomer mounting structure holding a motor in place, may be tuned to direct or dampen the movement of the head portion in particular directions. A pivot point constraining the shaft may also affect the movement of the head portion.

Different oral hygiene accessories may be attached to the oral hygiene device for use in oral hygiene, for example, a toothbrush head, a flosser tip (composed of either a single filament or a plurality of filaments), a tongue cleaner/scraper, a prophy cup for polishing, or other oral hygiene accessories. Further, a base unit may be provided for storing and charging the oral hygiene device, as well as for conveniently storing the various dental accessories for use with the oral hygiene device.

In one aspect of the invention, a power oral hygiene device is disclosed having a main body with a handle portion and a head portion. A first vibratory means is positioned in the handle portion and a second vibratory means is positioned in the head portion. The oral hygiene device also has a power means for providing energy to the first vibratory means and the second vibratory means.

In another aspect of the invention, a power oral hygiene device with a first motor operating at a first frequency and a second motor operating at a second frequency is disclosed. The oral hygiene device has a power source for providing energy to operate the first motor and the second motor. The motors are selected such that a ratio of the first frequency generated by the first motor to the second frequency generated by the second motor is between 1.3 and 3.

Yet another embodiment of the invention disclosed is a power toothbrush having a main body with a handle portion and a head portion. A first vibratory motor positioned in the handle portion and a second vibratory motor positioned in the head portion. A power source is provided for providing energy to the first motor and the second motor.

A base unit for holding oral hygiene device is also disclosed. The base unit is composed of a carousel with a plurality of chambers and a carousel cover, which is positioned over and covers the carousel. A means for rotating the carousel underneath the carousel cover is also provided. The carousel cover has an outer surface containing an opening. Access to the chambers in the carousel is provided through the opening in the carousel cover. A portion of the carousel is also exposed through the opening in the carousel cover, allowing a user to engage and rotate the carousel.

In a further aspect of the invention, a tongue scraper is disclosed. The tongue scraper has a head with a first plurality of teeth arranged in a first row and a second plurality of teeth arranged in a second row, spaced apart from the first row. Each tooth in the first row is separated from adjacent teeth by a notch. Similarly, each tooth in the second row is separated from adjacent teeth by a notch. Each of the notches between the teeth in the first row is positioned directly opposite at least a portion of one of the teeth in the second row. In this manner, no part of a user's tongue is left unscraped when the tongue scraper is pulled in a straight line across the user's tongue.

Other features, utilities and advantages of various embodiments of the invention will be apparent from the following more particular description of embodiments of the invention as illustrated in the accompanying drawings and defined in the appended claims.

BRIEF DESCRIPTION OF THE DRAWINGS

FIG. 8 illustrates an isometric view of a motor mount in accordance with one embodiment of the present invention.

FIG. 9 illustrates a top view of a motor mount in accordance with one embodiment of the present invention.

FIG. 10 illustrates a sectional view of the motor mount of FIG. 9 in accordance with one embodiment of the present invention.

FIG. 11 illustrates a sectional view of the motor mount of FIG. 9 in accordance with one embodiment of the present invention.

FIG. 12 illustrates a bottom view of a motor mount in accordance with one embodiment of the present invention.

FIG. 24 illustrates a motor frame positioned along a longitudinal axis.

FIGS. 25A–C illustrate a motor mount with a first set of compression properties and the resulting impact of the motor mount on the movement of the base end and shaft of the motor frame in accordance with one embodiment of the present invention.

FIGS. 26A–C illustrate a motor mount with a second set of compression properties and the resulting impact of the motor mount on the movement of the base end and shaft of the motor frame in accordance with one embodiment of the present invention.

FIGS. 27A–C illustrate a motor mount with a third set of compression properties and the resulting impact of the motor mount on the movement of the base end and shaft of the motor frame in accordance with one embodiment of the present invention.

FIGS. 28A–B illustrate the movement of the base end and shaft of a motor frame resulting from a gap between the motor frame and the housing of an oral hygiene device in accordance with one embodiment of the present invention.

FIGS. 34–39 illustrate the effect of various types of motors on the movement of the head of the oral hygiene device in accordance with one embodiment of the present invention.

DETAILED DESCRIPTION OF THE INVENTION

The structures and functions of various embodiments of an oral hygiene device will now be described.

Structure of the Oral Hygiene Device

Figure 1:
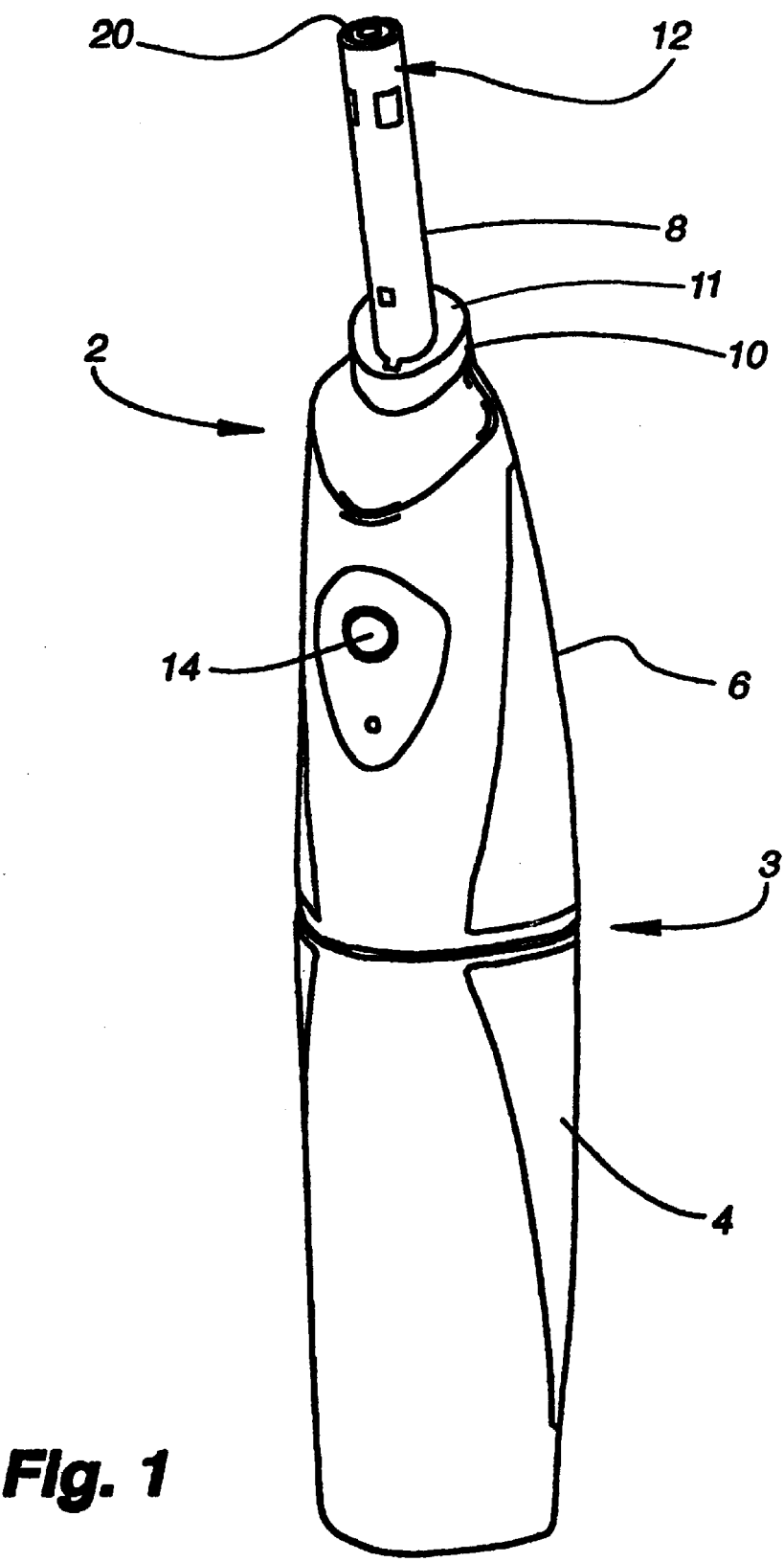
FIG. 1 illustrates an isometric view of an oral hygiene device in accordance with one embodiment of the present invention.
Figure 4:
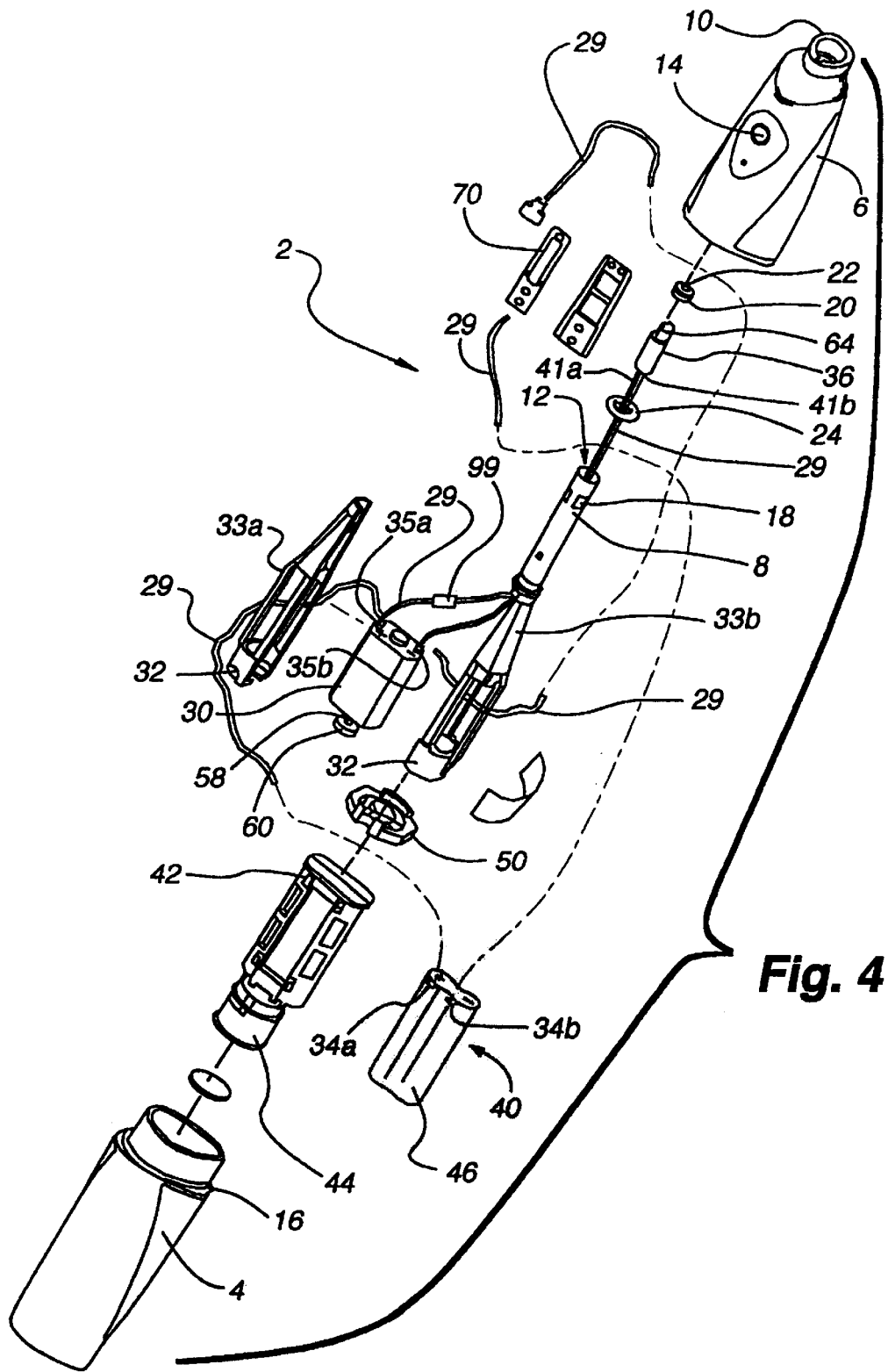
FIG. 4 illustrates an exploded view of an oral hygiene device in accordance with one embodiment of the present invention.

Referring to FIG. 1, an oral hygiene device 2 has a handle housing 3 composed of a lower handle housing 4 portion and an upper handle housing 6 portion, which form a body for the oral hygiene device 2. The upper handle housing 6 of the oral hygiene device 2 is adapted to securely fit about the mounting rim 16 of the lower handle housing 4 (as shown in FIG. 4).

Figure 5:
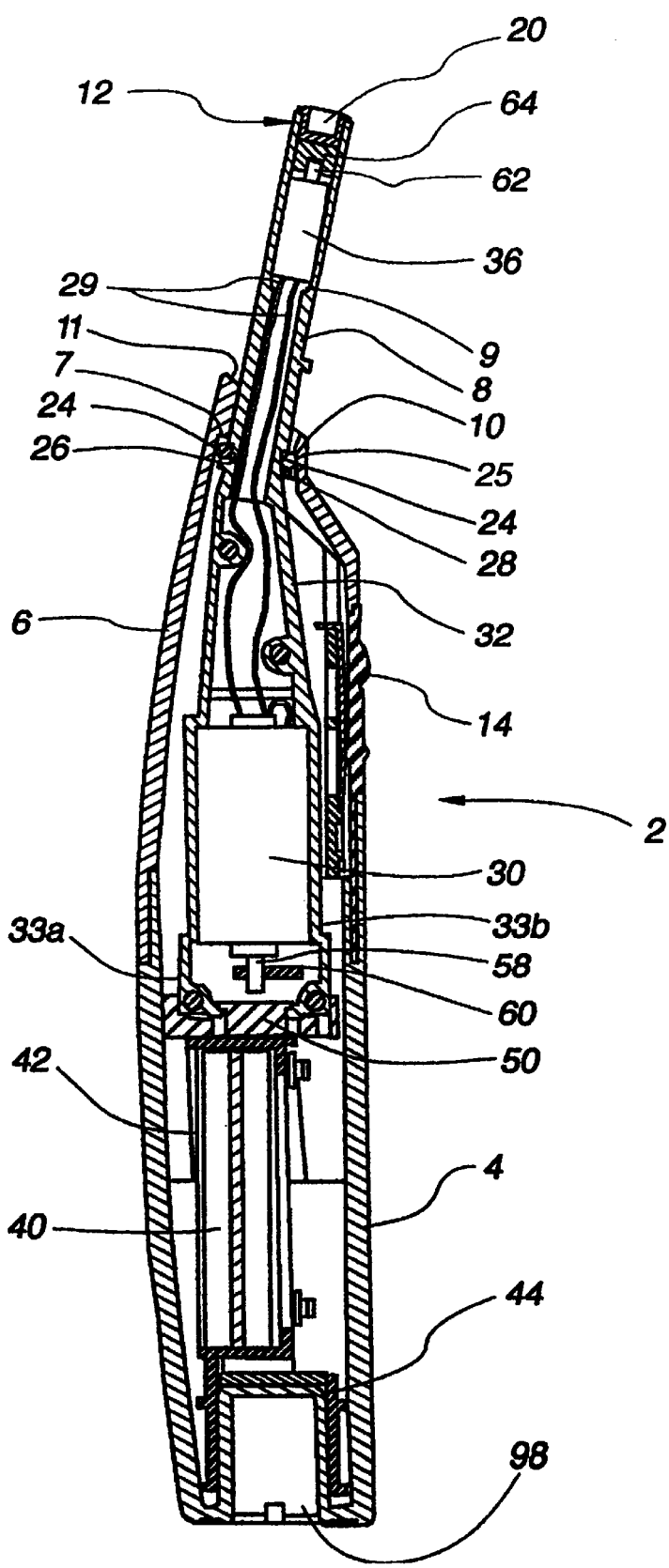
FIG. 5 illustrates a sectional view of an oral hygiene device in accordance with one embodiment of the present invention.

The head portion of the oral hygiene device 2 is built upon a shaft 8 extending from a annular shoulder 10 of the upper handle housing 6. The shaft 8 has a tip 12 to which various oral hygiene attachments 250 (see FIGS. 20–23A) can be removably secured. As shown in FIGS. 1 and 5, the annular shoulder 10 of the upper handle housing 6 forms a positioning sleeve for providing a desired relation between the upper handle housing 6 and the tip 12 of the shaft 8. As will be described in greater detail below, the oral hygiene device 2 has, in one embodiment, a primary motor 30 and a secondary motor 36, each operating at a different frequency to generate movement and vibration of the shaft tip 12 to provide for dental cleaning when used with the various oral hygiene attachments 250.

In order to achieve the desired vibration and movement of the shaft 8, the motors 30, 36 may be eccentrically weighted (i.e., a mass is mounted off-center on a motor shaft). The vibration caused by an eccentric mass motor is generally characterized by an orbital type of movement. The motor shaft may turn rotationally in one direction (e.g., clockwise or counter clockwise) or oscillate back and forth to create the orbital vibration. Other vibrational motors or devices that cause vibration, for example, piezo electric vibrational devices and motors creating axial, linear, or oscillatory vibration, are likewise contemplated for use in this invention.

The upper handle housing 6 has on its outer surface a pad or button 14 for receiving depressions by a thumb or a finger of a user of the oral hygiene device 2. As will be explained below, depending upon the implementation, when the user depresses the button 14, a switch 70 closes and power is applied to both motors 30, 36 so that the motors 30, 36 impart various vibratory frequencies to the tip 12 of the oral hygiene device 2. The switch 70 may allow the user to actuate either the primary motor 30 in the handle housing 3, the secondary motor 36 in the shaft 8, a combination of both, or even to alter the speed at which the motors 30, 36 operate.

Figures 2, 3:
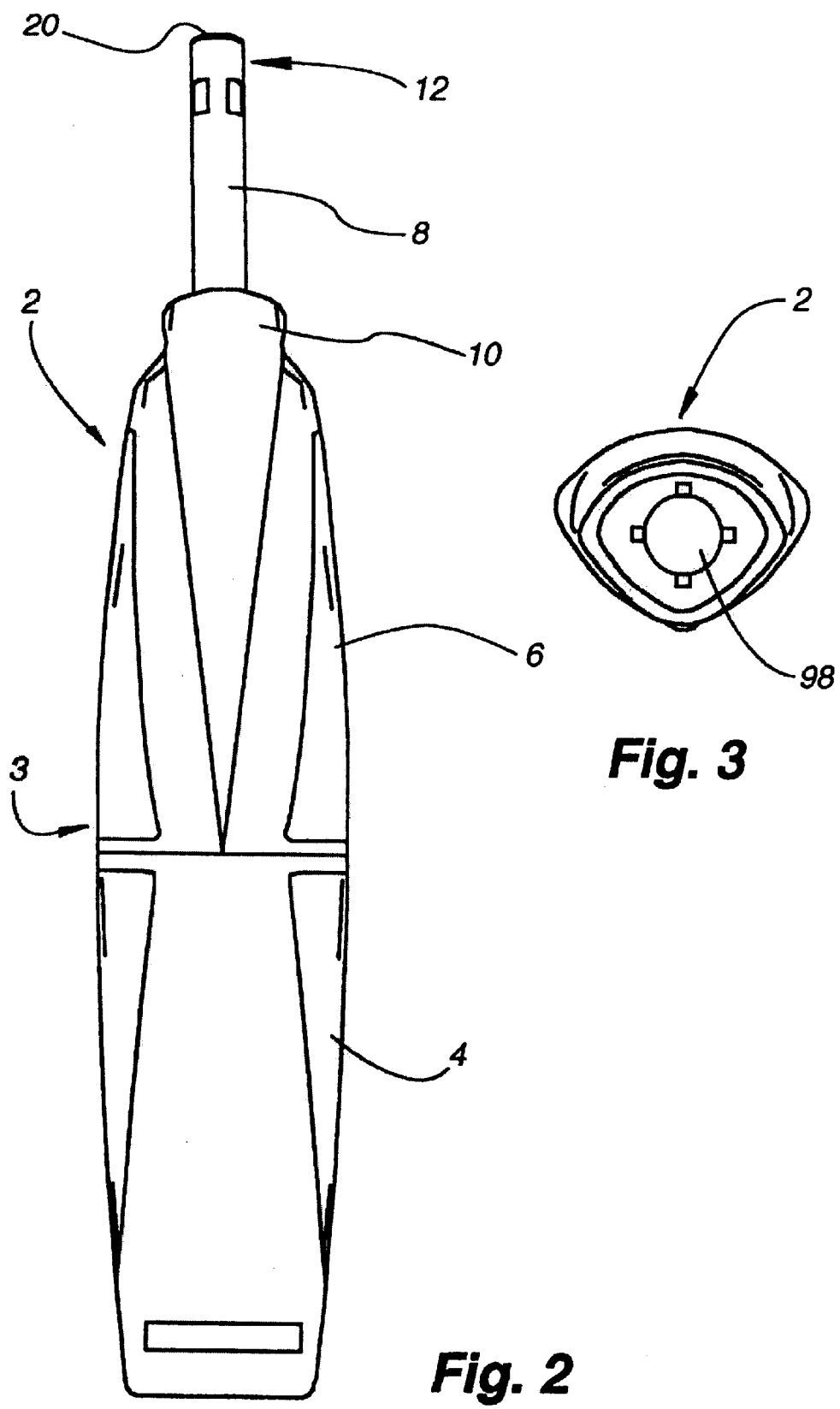
FIG. 2 illustrates a back side view of an oral hygiene device in accordance with one embodiment of the present invention.
FIG. 3 illustrates a bottom view of an oral hygiene device in accordance with one embodiment of the present invention.
Figure 15:
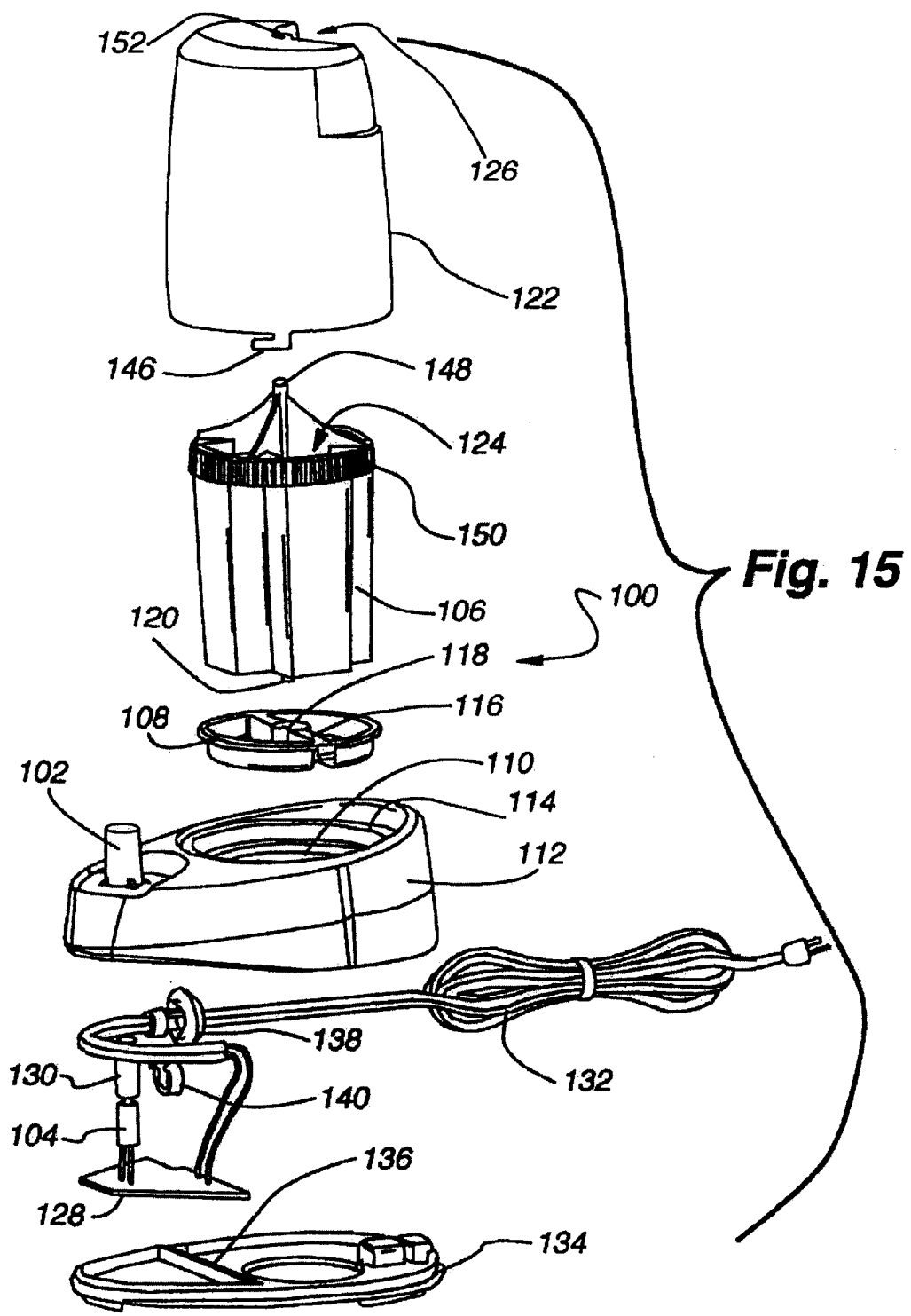
FIG. 15 illustrates an exploded view of a charging base for an oral hygiene device in accordance with one embodiment of the present invention.

Referring to FIG. 3, the oral hygiene device 2 has on its bottom end in the lower handle housing 4 a cavity 98 for capturing a post 102 of a charging unit 100 (as shown in FIG. 15) so that the oral hygiene device 2 can be stored and recharged if needed. The post capturing cavity 98 receives the post 102 to removably secure the oral hygiene device 2 on the charging unit 100.

Now referring to FIG. 4, an exploded view of an oral hygiene device 2 is shown in accordance with one embodiment of the present invention. A rechargeable battery 40 is positioned within a battery bracket 42 having a coil/magnet 44 combination attached thereto that can be used for charging the rechargeable battery 40, for example, when the oral hygiene device 2 is positioned within a charging unit 100 (as shown in FIG. 15). The coil/magnet 44, battery bracket 42, and battery 40 may be positioned substantially within the lower handle housing 4 of the oral hygiene device 2.

Figure 6:
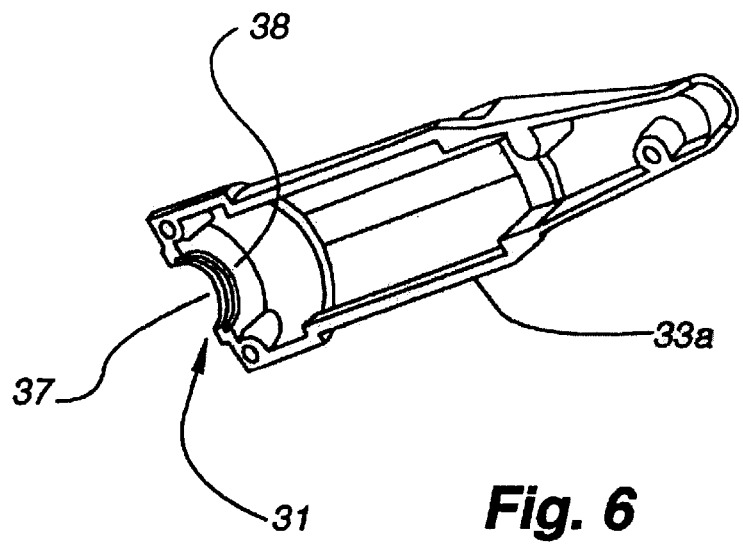
FIG. 6 illustrates an isometric view of a portion of a motor frame in accordance with one embodiment of the present invention.
Figure 7:
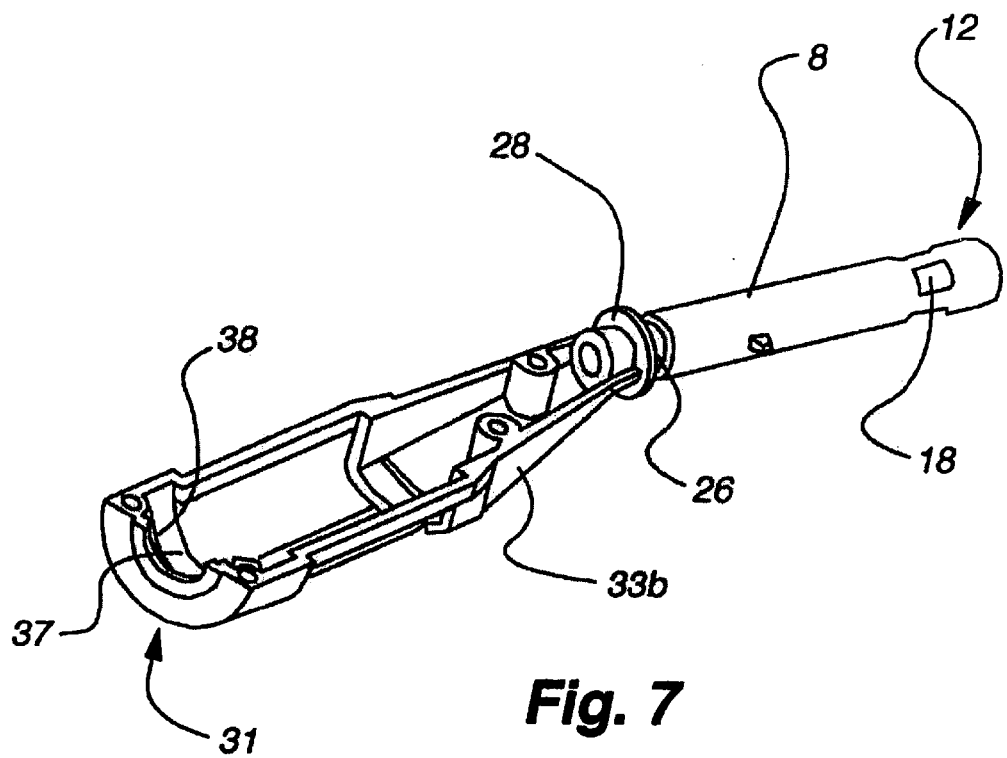
FIG. 7 illustrates an isomeric view of a portion of a motor frame having a shaft in accordance with one embodiment of the present invention.

The primary motor 30 may be positioned within a motor frame 32, as shown in FIG. 4. In one embodiment, the motor frame 32 is a two-piece structure (as shown in FIGS. 4, 6, and 7), which has a first motor housing portion 33a that is secured to a second motor housing portion 33b. The second motor housing portion 33b is attached to or formed integrally with the shaft 8, whereby the shaft 8 is actually part of the motor frame 32. The two-piece motor frame 32 snugly secures the primary motor 30 into a position within the motor frame 32. Therefore, when the primary motor 30 is activated, the vibratory force generated by the primary motor 30 is imparted to the motor frame 32, and thereby to the shaft 8. Both the first and second motor housing portions 33a and 33b of the motor frame 32 may be slotted along a portion of each side so that the wires 29 from the battery 40 may be connected to the primary motor 30 and further to the secondary motor 36 within the motor frame 32.

The shaft 8 may be integral with the motor frame 32 and outwardly protrude from the annular shoulder 10 of the upper handle housing 6. The shaft 8 of the motor frame 32 is generally cylindrical and receives the secondary motor 36 and the wires 29 within the interior of the shaft 8. As shown in FIG. 5, the shaft 8 may have tapered interior walls 9 defining an expanding (semi-conical) cylindrical cavity towards the tip 12 of the shaft 8, and an annular lip 11 interior to the shaft 8 to maintain the secondary motor 36 axially in position within the interior of the shaft 8. Similar to the action of the primary motor 30, the secondary motor 36 when activated imparts a vibratory force to the shaft 8 in which the secondary motor 36 is constrained. The vibrational force imparted by the secondary motor 36 to the tip 12 of the shaft 8 may be more vigorous than the force imparted by the primary motor 30 due to the proximity of the secondary motor 6 to the tip 12. An end cap 20 is inserted into the open end of the shaft tip 12 in order to provide a fluid-tight seal to preferably prevent fluids or other matter from entering the shaft tip 12 once the secondary motor 36 is positioned within the shaft 8.

An O-ring 24 is positioned within an annular channel 26 (as shown in FIG. 7) of the shaft 8. As shown in FIG. 5, when the motor frame 32 with the integral shaft 8 is positioned within the upper handle housing 6, the O-ring 24 is circumferentially constrained and may be compressed between an annular backplate 28 of the shaft 8 and an annular sealing shoulder 7 defined on the interior of the upper handle housing 6. The O-ring 24 may be made of silicone having a Shore hardness of approximately 40. The O-ring 24 is water resistant so that when secured around the shaft 8 and positioned within the upper handle housing 6, a fluid tight seal is formed which helps prevent water from entering into the cavity of the oral hygiene device 2.

At the base end 31 of the motor frame 32 proximate the primary motor 30, a motor mount 50 or anchor may be attached to the motor frame 32. The motor mount 50 may be provided in order to selectively regulate the movement of the primary motor 30 as it moves within the interior cavity of the oral hygiene device 2. The motor mount 50 is designed to fit tightly or snugly within the lower handle housing 4 of the oral hygiene device 2 (see FIG. 5). The cross-section of the motor mount 50 is sized to substantially match the interior cross-sectional shape of the lower handle housing 4 within and against which the motor mount 50 fits. The motor mount 50 also may dampen or isolate the vibrations of the primary motor 30 so as to reduce vibrations translated to the handle housing 3. Co-pending, co-owned U.S. application Ser. No. 10/045,953, entitled *Toothbrush with Motor Integrated with Vibrating Head*, filed Jan. 12, 2002, provides additional details with respect to vibration isolation structures and its entire contents are hereby incorporated by reference in their entirety as if fully disclosed herein. The motor mount 50 may be made of rubber or any suitable elastomer. In one example, the motor mount 50 may be made of a styrene-ethylene butylene-styrene material of an approximate Shore hardness of 40.

The motor mount 50 may have a central protrusion 52 with tabs 54 adapted to be positioned within an opening 37 at the base end 31 of the motor frame 32 (as shown in FIG. 7). Once the central protrusion 52 of the motor mount 50 is positioned within the opening 37, the tabs 54 help to maintain the attachment between the motor mount 50 and the motor frame 32 by extending over a shelf 38 at the base end 31 of the motor frame 32. The motor frame 32 may have a cross-sectional shape that is smaller than that of the handle housing 3. By suspending the primary motor 30, and the motor frame 32 around it, within the handle housing 3 by the O-ring 24 on the shaft 8 of the motor frame 32 and the motor mount 50 at the base end 31 of the motor frame 32, the transfer of vibration from the primary motor 30 to the handle housing 3 is dampened.

Oral Hygiene Attachments

Figure 20:
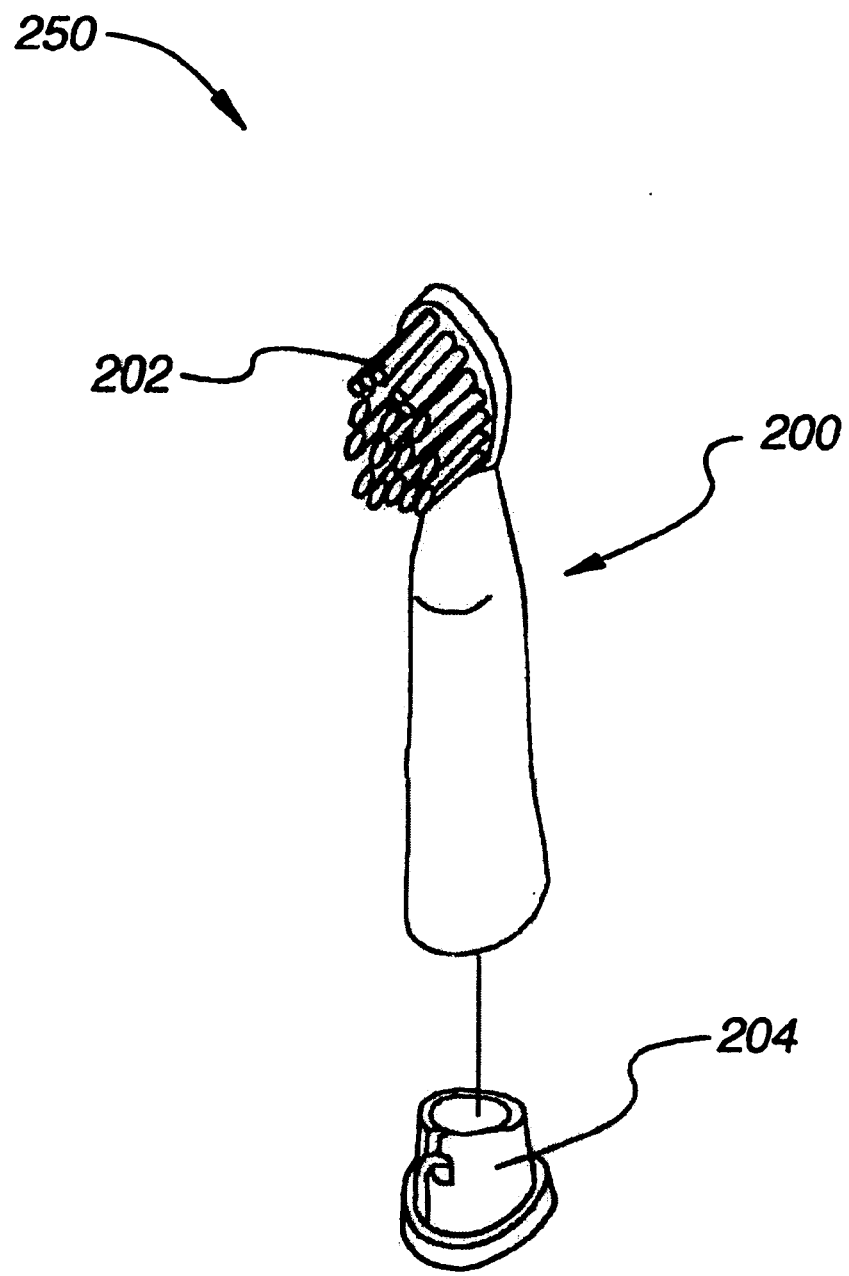
FIG. 20 illustrates an isometric view of a toothbrush attachment in accordance with one embodiment of the present invention.
Figure 21:
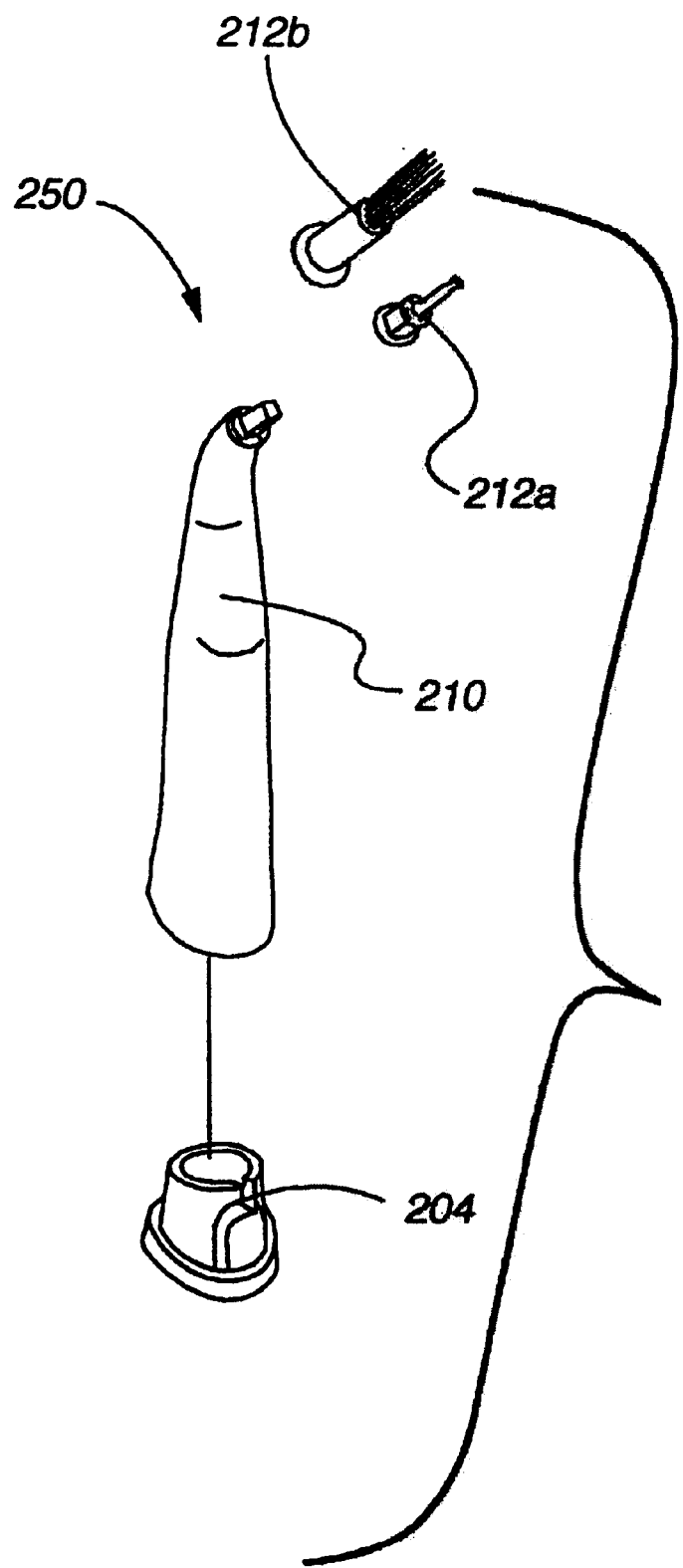
FIG. 21 illustrates an isometric view of a flosser tip/flosser head attachment in accordance with one embodiment of the present invention.

The tip 12 of the oral hygiene device 2 may be adapted to receive a plurality of different oral hygiene attachments 250. In this way, the oral hygiene device 2 can be used in different ways by a user to clean, polish, or otherwise service the user's teeth. For example, a brush head 200 having bristles 202 (as shown in FIG. 20) for brushing one's teeth may be connected with the end of the shaft 8 of the oral hygiene device 2. A flosser head 210 (having a flossing tip 212*a* with one filament or a flossing tip 212*b* with a plurality of filaments) (as shown in FIG. 21) may be connected with the end of the shaft 8 of the oral hygiene device 2 so that the user can floss with the oral hygiene device 2. Such flossing tips 212*a*, 212*b* are described in more detail in co-pending, co-owned application Ser. No. 09/883,013, *Tip for Dental Flossing Device*, filed Jun. 15, 2001, which is hereby incorporated by reference in its entirety as if fully set forth herein.

Figure 22:
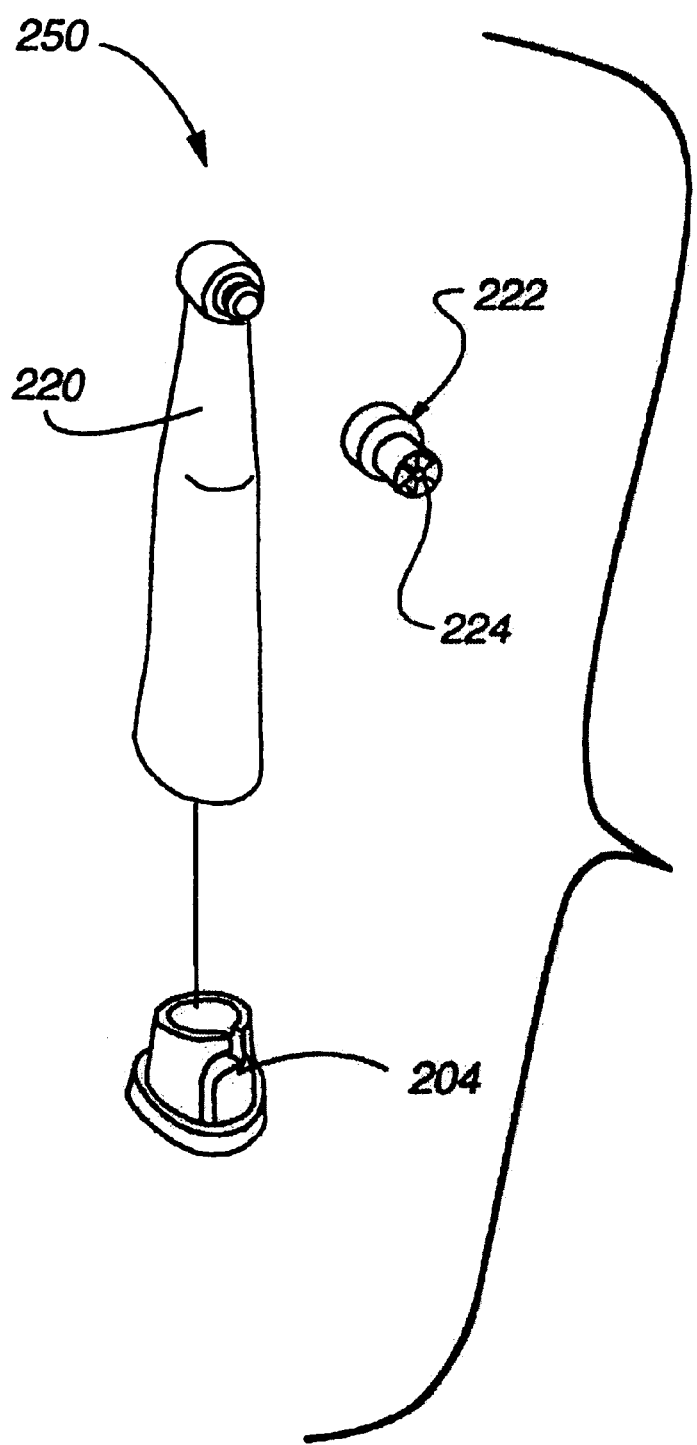
FIG. 22 illustrates an isometric view of a polishing cup head attachment in accordance with one embodiment of the present invention.

Alternatively, a polishing head 220 with a replaceable prophy polishing cup 222 (as shown in FIG. 22) can be connected with the end of the shaft 8 of the oral hygiene device 2, so that a user may polish teeth with the oral hygiene device 2. The prophy cup 222 includes a flexible cup-like head 224. During use, the cup-like head 224 is used to store dental paste for application to the user's teeth. The cup-like head 224 with paste is then pressed against the user's teeth to force the paste into the grooves, indentations, and spaces in and around the user's teeth. The cup-like head 224 is flexible so as to ensure no damage or discomfort is brought to the user or their teeth during use.

Figure 23A:
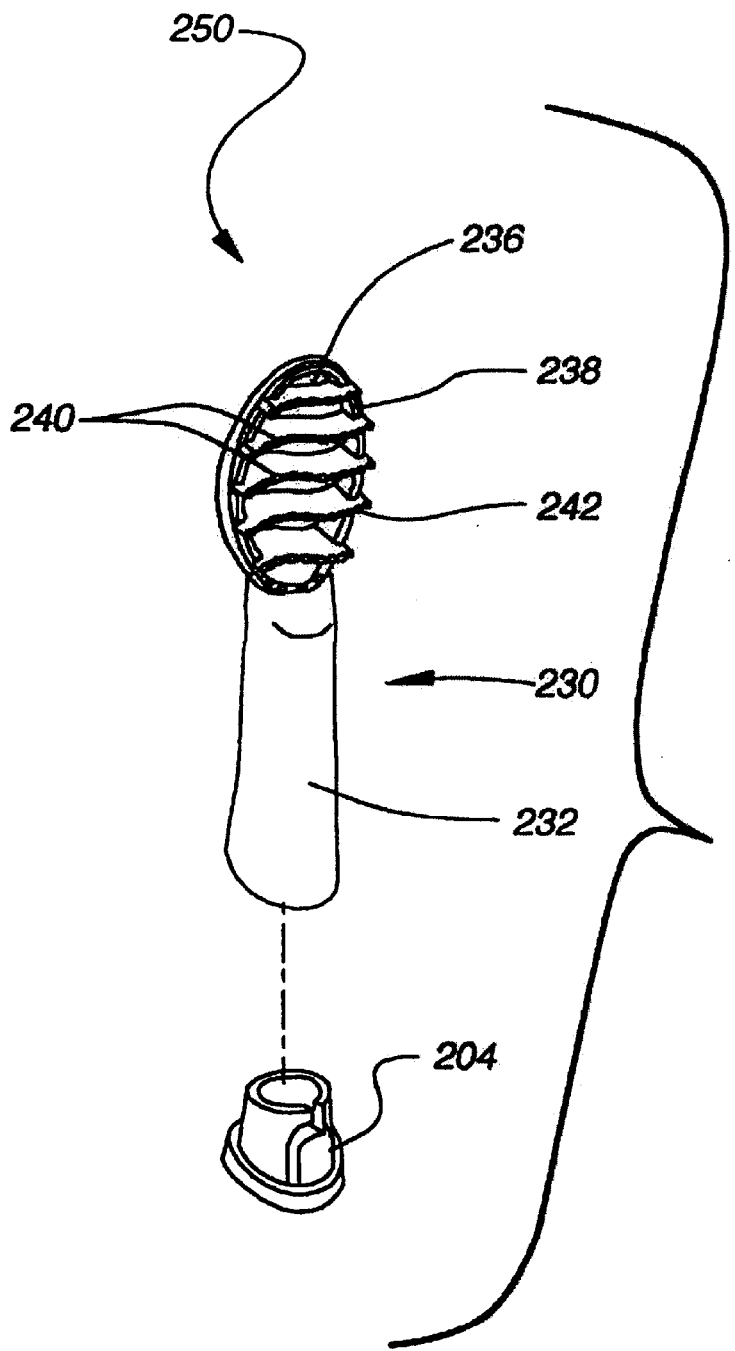
FIGS. 23A–H illustrate various views of a tongue cleaner attachment in accordance with one embodiment of the present invention.
Figures 23B, 23C, 23D, 23E:
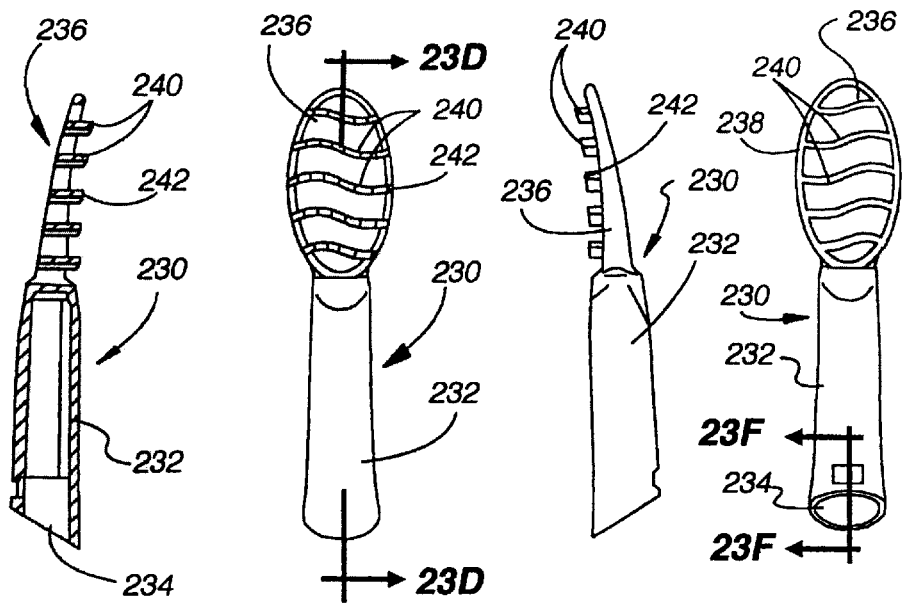
Figures 23F, 23G, 23H:
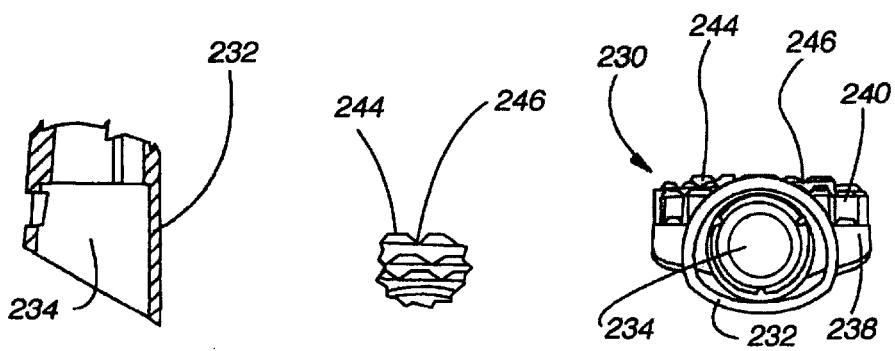

A tongue scraper 230, as shown in FIG. 23A, could also be attached to the shaft 8 so that a user could clean or scrape the tongue. The tongue scraper 230 for attachment to the oral hygiene device 2 of the present invention is shown in further detail in FIGS. 23B–H. This tongue scraper 230 has a sleeve 232 for attachment to the shaft tip 12 extending from the upper handle housing 6. FIGS. 23B and 23F show the attachment structure 234 used to affix this oral hygiene attachment 250 to the upper handle housing 6 of the oral hygiene device 2, which attachment structure 234 is representative of the structures used to attach the other oral hygiene attachments 250 to the oral hygiene device 2. The tongue scraper 230 has a head portion 236 that is formed by an oval frame 238 (as shown from the front in FIG. 23C and from the rear in FIG. 23E) extending with its major axis in line with the length of the sleeve 232. The oval frame 238 curves slightly forward (as shown in the cross section view of FIG. 23B and in the side view of FIG. 23E).

Ribs 240 extend laterally across the head portion 236 within the oval frame 238 (as shown in FIGS. 23C and 23E), and extend forwardly from the oval frame 238 (as shown in FIGS. 23B and 23D). Each rib 240 is curved in a symmetrical manner. The front edge 242 of each lateral rib 240 defines teeth 244 (which may have sloped edges) interspaced by notches 246 (which may be square or V-shaped). The teeth 244 on adjacent ribs 240 are aligned so that none of the notches 246 or teeth 244 are aligned longitudinally along the length of the tongue scraper 230 (as shown in FIGS. 23G and 23H). Thus, no part of the tongue under the tongue scraper 230 is left unscraped when the tongue scraper is pulled along its length (and thus along the tongue).

In one embodiment (best shown in FIG. 7), the tip 12 of the shaft 8 may have one or more slots 18, recesses, indentations, protrusions, or other attachment structures for securely receiving various oral hygiene attachments 250. The tip 12 of the shaft 8 may have an end cap 20, which may further have a dimple or other recess 22, so that an oral hygiene attachment 250 may be attached securely to the tip 12 of the shaft 8 of the oral hygiene device 2. Generally, a detent structure is used to snap-fit the oral hygiene attachment 250 to the tip 12 of the shaft 8. Each oral hygiene attachment 250 fits entirely over and around the shaft 8 and a bottom portion engages the annular shoulder 10. In one embodiment, a color coded band 204 may be snap fitted into the bottom of the sleeve 232 to identify oral hygiene attachments 250 of different users.

Base Charging Unit

Figure 16:
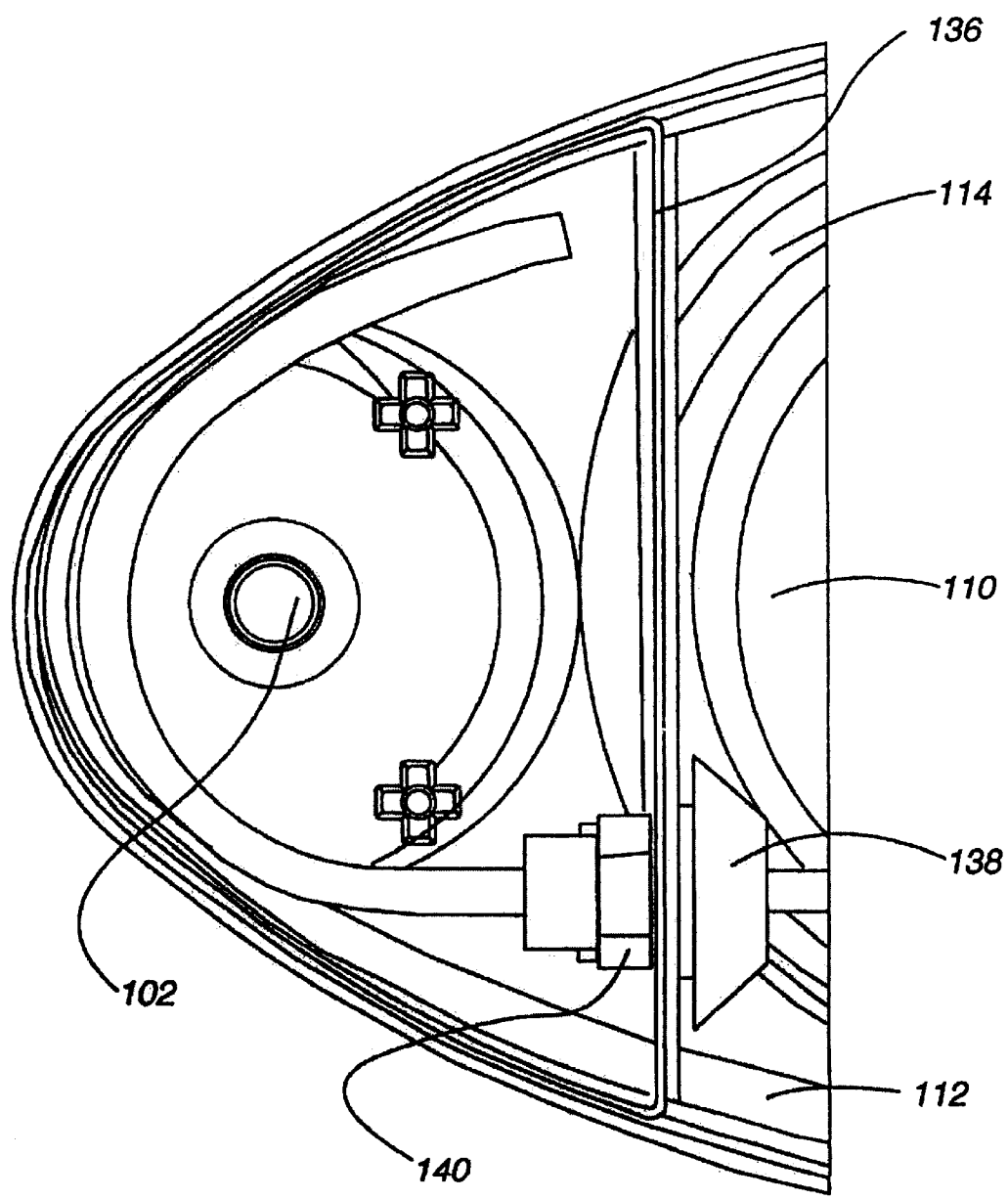
FIG. 16 illustrates a bottom view of a portion of the upper housing portion of the charging base of FIG. 15 in accordance with one embodiment of the present invention.
Figure 17:
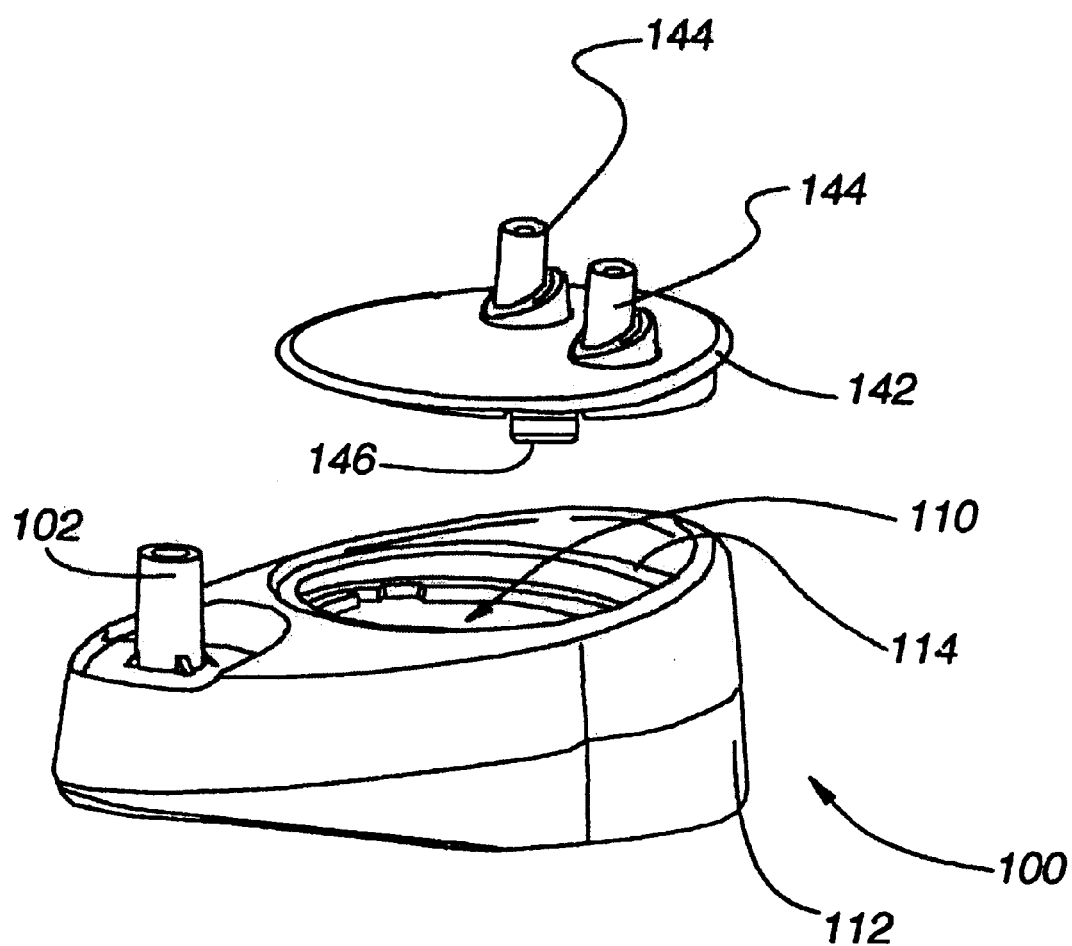
FIG. 17 illustrates an alternative embodiment of a cover for a charging base in accordance with one embodiment of the present invention.

FIGS. 15–17 illustrate a base charging unit 100 for storing the oral hygiene device 2 and the various oral hygiene attachments 250. Further, the base charging unit 100 may include circuitry to provide a charging voltage to the oral hygiene device 2 when the oral hygiene device 2 is placed about the charging post 102 of the base charging unit 100.

As shown in FIG. 15, the base charging unit 100 can be provided with a carousel 106 mounted above a drip cup 108, which is positionable within a cylindrical cavity 110 of the upper housing 112. An annular support ledge 114 of the upper housing 112 supports the drip cup 108 and carousel 106 when positioned in the upper housing 112. The drip cup 108 has a divider 116 with a central recess 118 for accepting a protrusion 120 from the carousel 106 so that the carousel 106 can be removably secured onto the drip cup 108.

A carousel cover 122 fits over the carousel 106 and may be removably secured to the upper housing 112 of the base charging unit 100 by detents 146. The carousel cover 122 may have a small aperture 152 or indention in its top surface to receive a nub 148 on the top of the carousel 106 to aid in the alignment of the carousel 106 with the carousel cover 122. The carousel 106 has a plurality of chambers 124 separated by walls for storing tips or other oral hygiene attachments 250 for the oral hygiene device 2. The drip cup 108 collects any fluids which may drain from the oral hygiene attachments 250 stored in the carousel 106. In one embodiment, each chamber 124 of the carousel 106 has a floor (not shown) upon which rests any oral hygiene attachment 250 stored in the chamber 124. The floor in each chamber 124 has at least one aperture (not shown) for allowing any fluid therein to drain into the drip cup 108. The aperture(s) may be, for example, perforations or conical holes.

The carousel cover 122 has an opening 126 along a portion of its top surface and upper side wall so that a user can deposit oral hygiene attachment 250 tips into or remove them from the carousel 106. Once the drip cup 108, carousel 106, and carousel cover 122 are removably secured within the cylindrical cavity 110 of the upper housing 112, a user can rotate the carousel 106 within the cover 122 by engaging the knurled edge 150 of the carousel 106 exposed in the opening 126 with a finger. The central recess 118 in the drip cup 108 acts as a bearing within which the protrusion 120 of carousel 106 rotates. The user can rotate the carousel 106 until a desired chamber 124 becomes aligned with the opening. The user may insert or remove tips or other oral hygiene attachments 250 for the oral hygiene device 2 into any desired chamber 124, and then rotate the carousel 106 until the filled chamber 124 is covered by the carousel cover, thus protecting the oral hygiene attachments 250.

In one embodiment, the carousel cover 122, the carousel 106, and the drip cup 108 are removable from the upper housing 112 so that a user may remove these elements and wash them, for instance, using a dishwasher. The drip cup 108, carousel 106, and carousel cover 122 may be made of dishwasher safe material, for example, ABS (acrylonitrile butadiene styrene).

The upper housing 112 also has a charging post 102 for engaging a charging post capturing cavity 98 in the bottom end of the oral hygiene device 2 when the user places the oral hygiene device 2 on the charging post 102 for storage or for charging. The charging post 102 contains, in its interior, a cylindrically shaped charging coil 104, which is electrically coupled with a base circuit board assembly 128. The charging coil 104 may be covered with electrical tape 130 if desired. The base circuit board 128 may have circuitry to condition the line voltage received from the AC line power cord 132. In one embodiment, the base circuit board 128 contains circuitry easily adaptable at manufacturing to accommodate different line voltages, for example, 100 volts AC at 50 hertz, 120 volts AC at 60 hertz, 230 volts AC at 50 hertz, or other line voltages. In one embodiment, the charging coil 104 provides a 50,000 hertz AC signal to create an electromagnetic field about the charging coil/magnet 44 of the oral hygiene device 2.

The base circuit board 128 may also have an LED (not shown) on its bottom side in order to illuminate the lower housing 134 of the base charging unit 100 if the lower housing 134 is made of translucent or clear material. In this manner, the LED can provide visual indication that the base charging unit 100 is receiving a line voltage.

As shown in FIG. 16, the upper housing 112 and lower housing 134 have walls 136 defining an area for housing the base circuit board 128. In one embodiment, the wall 136 of the upper housing 112 has an opening to receive the electrical cord 132, which is connected with the base circuit board 128. A grommet 138 may be used to secure the electrical cord 132 within the opening within the wall 136 of the upper housing 112. The grommet 138 may provide a water seal and strain relief for the electrical cord 132. On the opposing side of the wall 136 from the grommet 138, a clip 140 can be used to further secure the electrical cord 132 to the wall 136. The area defined within the interior of the base charging unit 100 between the upper housing 112 and lower housing 134 may be used for storage of the electrical cord 132.

FIG. 17 illustrates an alternative embodiment of the base charging unit 100, wherein a cover 142 has a plurality of posts 144 (two posts are shown in this example). The cover 142 may be adapted to be removably secured within the cylindrical cavity 110 of the upper housing 112. These additional posts 144 can be used to store additional accessories or oral hygiene attachments 250 for the oral hygiene device 2.

Motors and Basic Circuit

In one embodiment, as shown in FIGS. 4 and 5, the primary motor 30 is a direct current motor operating on an input voltage of approximately 2.4 volts and at this voltage rotates at approximately 14,000 RPM. An eccentric mass 60 is attached to the shaft 58 of the primary motor 30, wherein the eccentric mass 60 is attached to the motor shaft 58 at a location off the center of mass of the eccentric mass 60, thereby creating inertia, which causes the primary motor 30, and thus the structure to which the primary motor 30 is attached, to vibrate. The eccentric mass 60 may be, for example, a brass casting, of SAE standard 72, half hard temper, with a mass of approximately 0.65 g. One exemplary motor meeting this criteria is manufactured by Mabuchi Motor Company, Matsudo City, Japan, model no. FK-130SH-3040.

The secondary motor 36 is, in one embodiment, capable of rotating at 5,000–9,000 RPM, and operating on approximately 1.2 volts DC. The secondary motor 36 may have an eccentric mass 64 attached to its motor shaft 62 so that as the eccentric mass 64 rotates, the secondary motor 36 vibrates within the shaft 8 of the oral hygiene device 2, thereby imparting a second frequency or set of frequencies of vibration on the shaft 8 of the oral hygiene device 2. In another embodiment, the secondary motor 36 may operate on approximately 2.4 volts DC. One exemplary motor meeting this criteria is manufactured by Jinlong Machinery & Electronics Company, Ltd., China, model no. 6CL-14WB27.

The vibrational frequencies contemplated by the dual motor design range from subsonic frequencies through ultra-high frequencies depending on the type of motor. For example, an eccentric mass motor may have a frequency of rotation of 300 to 15,000 RPMs while a peizo vibrational motor may have a vibrational frequency of 20,000 hertz or higher. In one embodiment, the ratio of operating frequency between the primary motor 30 and the secondary motor 36 is between approximately 1.3 and 3. This ratio of frequencies has been found to provide the desired level of interference to create pseudo-random, chaotic, motion. The beneficial frequency ratio can vary based on the relative positions of the motors 30, 36 in the oral hygiene device 2, as well as the structural characteristics associated with the attachment of the motors 30, 36 to the oral hygiene device 2.

As shown in FIGS. 4 and 5, each of the motors 30, 36 are positioned so the motor shafts 58, 62 are aligned along a common or nearly common axis. As shown in FIG. 34, however, the motors 30, 36 may be oriented in the oral hygiene device 2 so the motor shafts 58, 62 extend along axes A and B offset from one another. In FIG. 34, the secondary motor 36 is oriented such that the rotation of the eccentric mass 64 causes an oscillatory, orbital vibrational movement, and the primary motor 30 is mounted such that the axis B of rotation of its motor shaft 58, and corresponding vibration, is at an angle offset from axis A of the secondary motor 36. In FIG. 34, the axis B of rotation of the primary motor 30 is offset approximately 90° from the axis A of rotation of the secondary motor 36. In other embodiments, this offset angle may be less than or greater than 90°. Depending on the frequency and the amplitude of vibration, this combination of motor orientation can create a greater three-dimensional movement of the tip 12, as opposed to the primarily two-dimensional motion of the tip 12 in the embodiment of FIG. 5.

A battery pack 46 may be provided to house two AAA rechargeable batteries 40 in series, thereby providing a power source of 2.4 volts to drive both motors 30, 36. As shown in FIG. 4, a positive lead 34a from the battery pack 46 is coupled with the positive lead 35a of the primary motor 30. The positive lead 35a of the primary motor 30 is coupled through a resistor 39 to the positive lead 41a of the secondary motor 36. The resistor 39 may be sized to reduce the voltage applied to the positive lead 41a of the secondary motor 36 to approximately 1.2 volts. In one embodiment, the resistor 39 may provide a resistivity of 0.62 ohms. In other embodiments, the secondary motor 36 may operate on the same voltage as the primary motor 30 and, therefore, the resistor 39 would be unnecessary. In order to complete the circuit, the negative lead 34b from the battery pack 46 is coupled with a first end of a switch 70, while a second end of the switch 70 is coupled with the negative terminal 35b of the primary motor 30, which is also coupled with the negative terminal 41b of the secondary motor.

In this manner, when the switch 70 is closed by the user pressing the button 14, a voltage of approximately 2.4 volts is applied across the terminals of the primary motor 30, and a voltage of approximately 1.2 volts is applied across the terminals of the secondary motor 36 by using resistor 99 to decrease the voltage from the battery 40. In the embodiment shown in FIG. 4, the switch 70 utilized may be a single-pole, single-throw switch, which does not change state until it is depressed again by a user. If the switch 70 is closed, when the user again presses the button 14, the switch 70 opens and the circuit shown in FIG. 4 is open, thereby removing power from the motors 30, 36 and turning off the oral hygiene device 2.

In one embodiment, when the user depresses the button 14, power is applied to the primary motor 30 and secondary motor 36 and each begins to rotate its respective eccentric mass 60, 64 about each motor shaft 58, 62. Accordingly, the primary motor 30 moves the shaft 8 of the oral hygiene device 2 relative to the O-ring 24 at approximately the frequency at which the primary motor 36 revolves about the pivot point 25 as limited by the motor mount 50. In this manner, the primary motor 30 imparts a fundamental vibration to the tip 12 of the shaft 8, for example, an orbital motion about a longitudinal axis. In addition, the secondary motor 36 also imparts a vibration to the tip 12 of the shaft 8 at a slower or faster frequency, as desired.

Logic-Based Circuit

Figure 13:
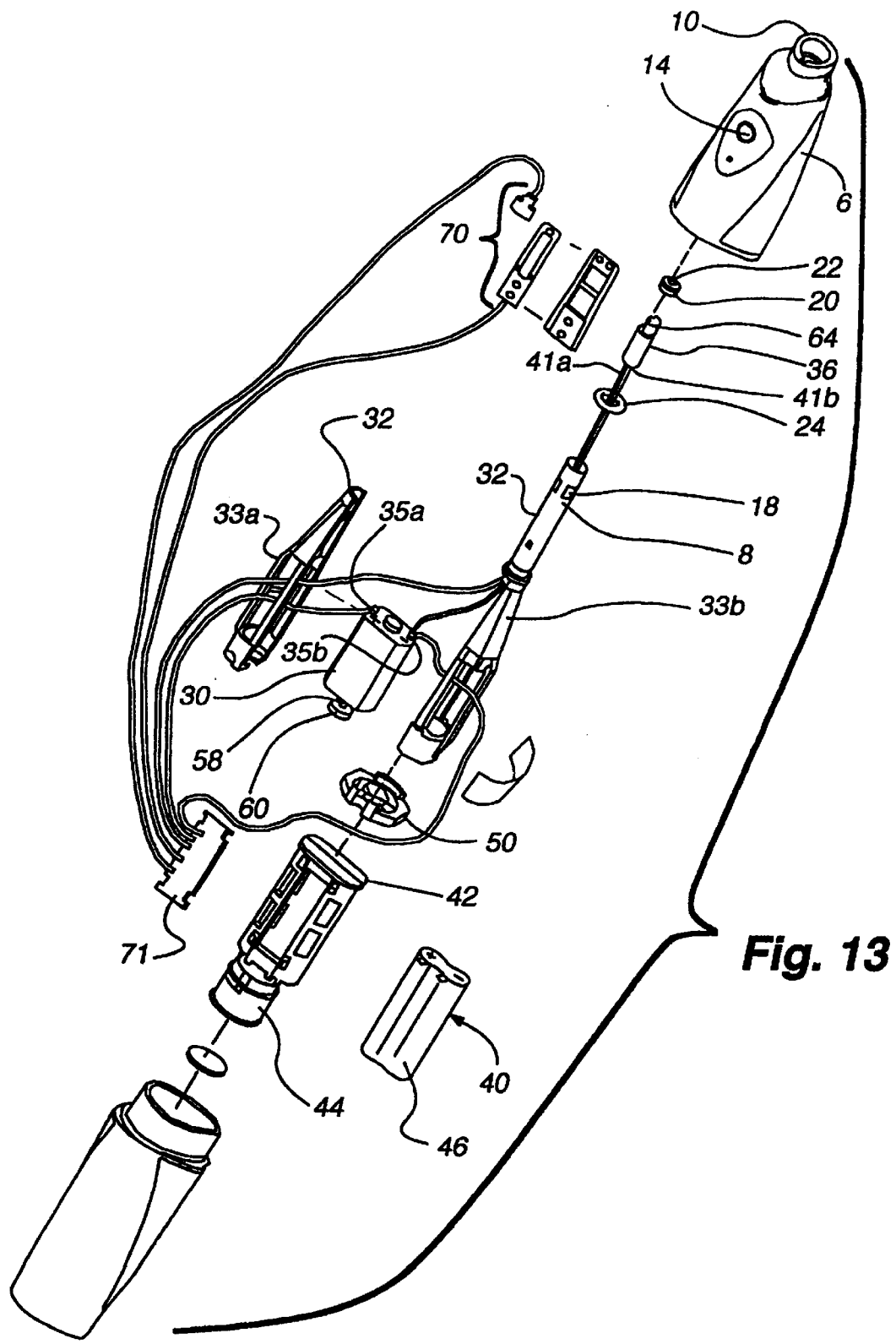
FIG. 13 illustrates an exploded view of an oral hygiene device having a circuit board for controlling the oral hygiene device in accordance with one embodiment of the present invention.
Figure 14A:
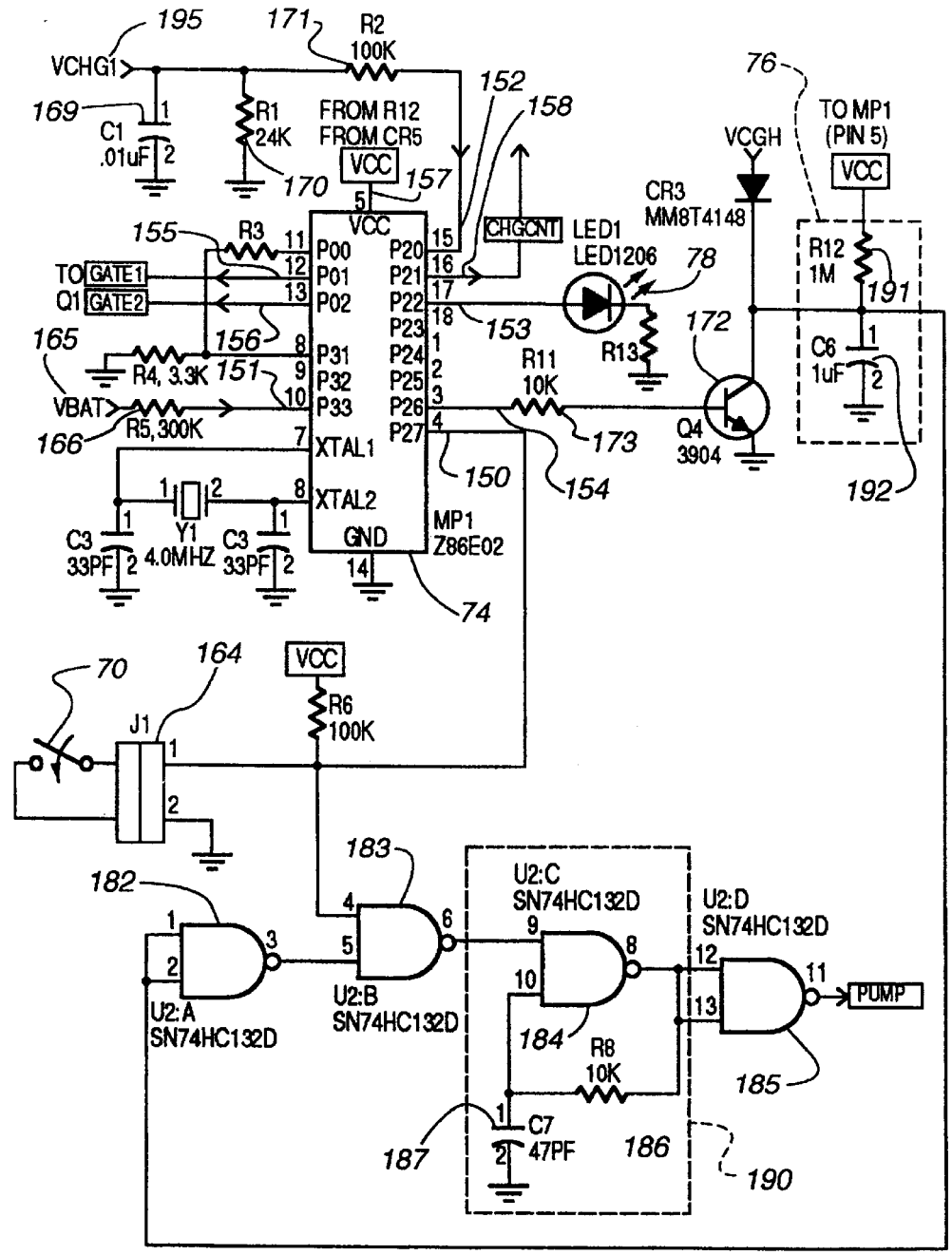
FIGS. 14A–B illustrate a circuit for controlling an oral hygiene device in accordance with one embodiment of the present invention.
Figure 14B:
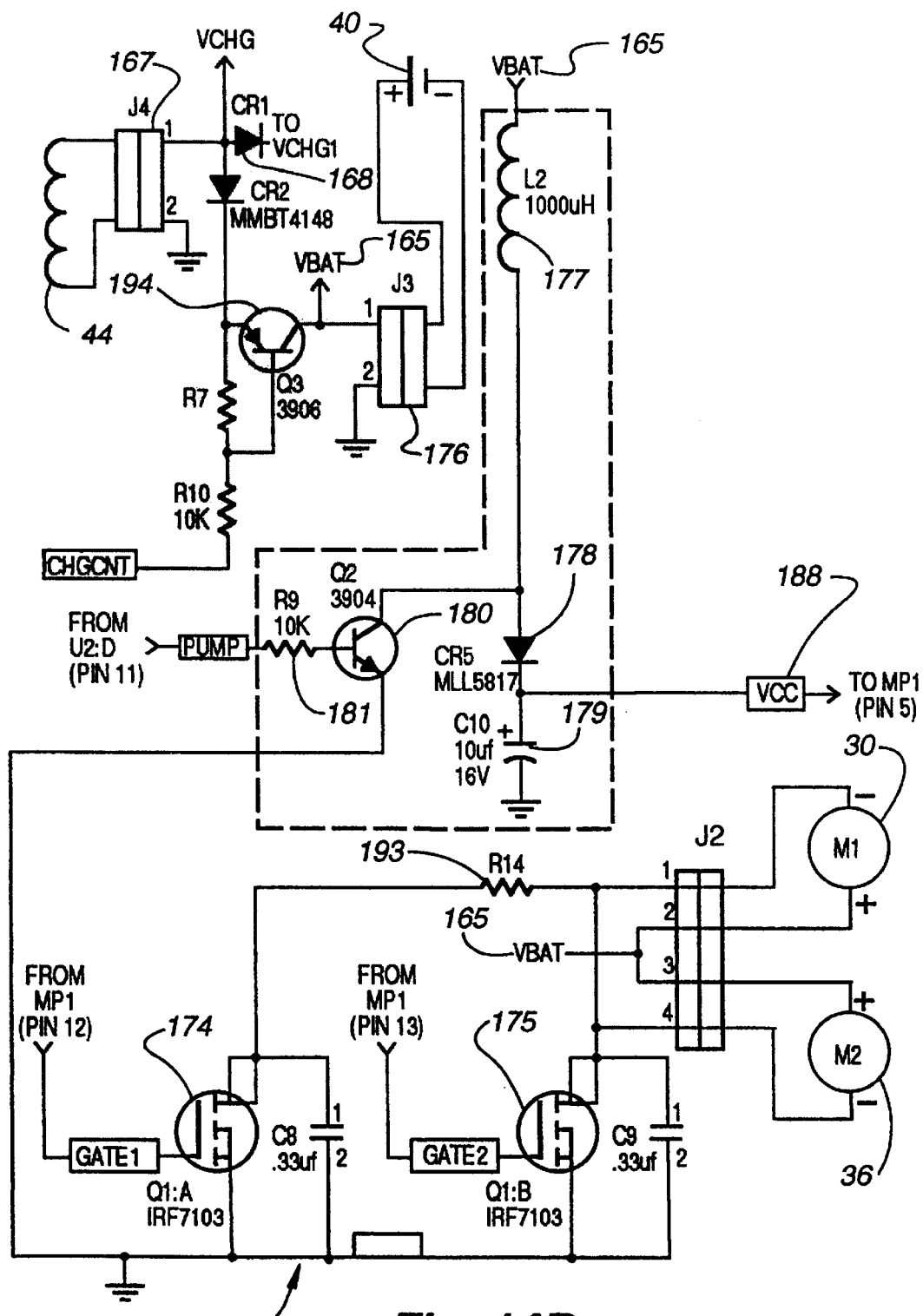

In another embodiment, as shown in FIG. 13, a printed circuit board 71 is attached to the battery bracket 42. The printed circuit board 71 includes a circuit 72 (see FIGS. 14A and 14B) for controlling the operations of the oral hygiene device 2. A microprocessor 74 (see FIGS. 14A and 14B) or other logic device may be provided as part of the circuit 72 to selectively control the operations of the oral hygiene device 2. The microprocessor 74 may be a processor, microcontroller, or other programmable logic device having configurable input/output (I/O) pins operating under the control of a software program stored within the microprocessor 74 or external to the microprocessor 74. FIGS. 14A and 14B illustrate one example of a circuit 72 that may be incorporated into an oral hygiene device 2 of the present invention. In this embodiment, the circuit 72 is provided for controlling the operations of the primary motor 30 and the secondary motor 36 in response to various conditions, for example, user input (depression of the button 14), battery voltage, battery recharging, or other conditions.

Generally, when the user depresses the button 14 to activate the oral hygiene device 2, the microprocessor 74 activates the primary motor 30 to operate at a lower speed mode of approximately 9,000–10,000 rpm, for example. The secondary motor 36 is also activated to operate at approximately 6,000 rpm, for example. If, during this "low speed" mode operation, the user depresses the button 14 again, then the microprocessor 74 activates a "high speed" mode wherein the voltage applied to the motors 30, 36 is increased so that the primary motor 30 and secondary motor 36 rotate at higher speeds, for example, 13,000–14,000 rpm and 9,000 rpm, respectively. If, during the "high speed" mode, the user depresses the button 14 again, then the microprocessor 74 disables both the primary motor 30 and secondary motor 36 and turns off the oral hygiene device 2. While FIG. 14B shows the primary motor 30 and the secondary motor 36 connected in parallel, it is possible to configure the circuit 72 so that each motor 30, 36, and thereby the speed of each motor 30, 36, is separately controlled by the microprocessor 74.

The microprocessor 74 may be further configured to support an automatic shut-off, for example, after 3 minutes of operation. This automatic shut-off function may be implemented by maintaining a timer, which may be programmed within or external to the microprocessor 74. The timer may be initiated upon the detection of the user initially depressing the button 14, and the timer may be stopped either after the user turns off the oral hygiene device 2, or the microprocessor 74 detects that the battery 40 is charging. If the timer expires after the 3 minutes, the microprocessor 74 turns off the motors 30, 36.

If the microprocessor 74 detects that the battery 40 is charging (e.g., after the user has inserted the oral hygiene device 2 into a base charging unit 100 (see FIG. 15)), the microprocessor 74 may illuminate an LED 78 to indicate that charging is occurring. If the oral hygiene device 2 is operating at the time that the oral hygiene device 2 is inserted into the base charging unit 100, the microprocessor 74 may disable both motors 30, 36 so that the oral hygiene device 2 shuts off.

The microprocessor 74 may also support a timer program, which periodically removes power from the motors to provide the user with an indication of the expiration of a time period, for example, a 30 second interval. The microprocessor 74 may, after 30 seconds of operation, disable the power applied to the motors 30, 36 for a short period of time (e.g., 1 to 2 seconds) then reapply power to the motors 30, 36 so that the user is made aware that the oral hygiene device 2 has been operating for 30 seconds. In an alternate embodiment, the power may be interrupted to only the primary motor 30, or to only the secondary motor 36, thus changing the vibratory effect felt by a user, as the indication of the expiration of the time period. In this way, the user can utilize the oral hygiene device 2 on a quadrant of the user's mouth, for example, and then shift the focus of the dental cleaning to another section or quadrant of the user's mouth upon the expiration of the 30 second timer.

The microprocessor 74 may receive a variety of inputs, for example, a switch input 150 (receiving a signal from the switch 70 via connector J1 (164) coupled with input pin 4 (150) of microprocessor 74); a battery level sense input 151 (receiving a signal from the line voltage of the battery 40 at VBAT (165) coupled through a resistor R5 (166) into input pin 10 (151) of the microprocessor 74); and charging coil voltage sense input (152) (receiving a signal from pin 1 of connector J4 (167) through diode CR1 (168) into the circuit of capacitor C1 (169), resistor R1 (170), and resistor R2 (171) coupled with input pin 15 (152) of microprocessor 74) to detect the presence of the charging coil 104 of the base unit 100 (see FIG. 15). In one variation, the switch 70 used in the embodiment of FIG. 14A may be a momentary switch.

The microprocessor 74 outputs may include, for example, an LED output 153 for controlling the illumination of a visual indicator, such as an LED 78 (shown as output pin 17 (153) of the microprocessor 74 driving LED1 (78)); a timer output 154 for controlling a timer circuit 76, which is used to activate a voltage boost circuit (shown as output pin 3 (154) of the microprocessor 74 driving the base of transistor Q4 (172) through resistor R11 (173)); a first motor 30, 36 control output 155 to control the application of a voltage level to the motors 30, 36 (for example, shown as output pin 12 (155) driving the gate of transistor Q1:A (174) to provide a low speed voltage to the motors 30, 36); and a second motor control output 156 to provide a second voltage signal to the motors 30, 36 (shown in this example as output pin 13 (156) of the microprocessor 74 driving the gate of transistor Q1:B (175) in order to provide a voltage for high speed operation of the motors 30, 36).

Referring to FIG. 14B, the terminals of the battery 40 are coupled with the circuit 72 through connector J3 (176), and pin 1 from connector J3 (176) establishes the battery voltage signal VBAT (165) used through the circuit 72. In one embodiment, the batteries 40 used may be nickel metal hydride batteries, which provide a longer life compared to nickel cadmium (Nicad) batteries. Further, nickel metal hydride batteries do not need to be recycled and can be disposed of by the end user. However, a Nicad battery or other rechargeable battery or power source may also be used as another embodiment of the invention. As described above, the batteries 40 may be, for example, two AAA rechargeable batteries connected in series to provide a voltage of approximately 2.4 volts.

One embodiment of the circuit 72 includes a switching power supply, which boosts the voltage of the battery 40 from approximately 2.4 volts to a level of approximately 5 volts, for example. The VBAT (165) signal may be boosted using a boost circuit 189 comprised of inductor L2 (177), diode CR5 (178), capacitor C10 (179), transistor Q2 (180), and resistor R9 (181). An oscillator 190 formed by NAND gate U2:C (184), resistor R8 (186), and capacitor C7 (187) drives the boost section 189 to boost the voltage from the battery 40 to approximately 5 volts as measured between point VCC (188) and ground, as shown in FIG. 14B, by microprocessor 74 at input pin 5 (157), as shown in FIG. 14A.

Accordingly, when the microprocessor 74 sets output pin 3 (154) high, transistor Q4 (172) is actuated and sets the input of NAND gate U2:A (182) low so that input pin 5 of NAND gate U2:B (183) is set high. Assuming the push button 14 is not depressed to actuate switch 70 at this time, then input pin 4 of NAND gate U2:B (183) is also set high, so that the output of NAND gate U2:B (183) is low, which disables the oscillator (190) (formed by NAND gate U2:C (184), resistor R8 (186), and capacitor C7 (187), in this example). Since the oscillator 190 is disabled, the boost section 189 of the circuit 72 is also disabled because the pump signal output of NAND gate U2:D (185) applied to the base of transistor Q2 (180) is low.

In another embodiment of the circuit 72, the microprocessor 74 sets output pin 3 (154) high before entering a sleep mode. In this manner, the microprocessor 74 turns off the oscillator 190 and voltage boost section 189 of the circuit 72 before entering the sleep mode. The RC timer 76 formed by resistor R12 (191) and capacitor C6 (192), however, will begin charging after the microprocessor 74 enters the sleep mode and transistor Q4 (172) turns off. The values of resistor R12 (191) and capacitor C6 (192) may be selected to provide approximately 1 second charging time, whereby after the microprocessor 74 has been asleep for approximately 1 second, the charge on the capacitor C6 (192) is high enough to switch NAND gate U2:A (182) to a low output. When the output of NAND gate U2:A (182) is low, the output of NAND gate U2:B (183) switches high, which actuates the oscillator 190 circuit. When the oscillator 190 is actuated, the voltage boost section 189 is also actuated and the signal VCC (188) increases from approximately 2.4 volts to approximately 5 volts, as described above.

If the microprocessor 74 detects that the supply voltage has been boosted to approximately 5 volts, the microprocessor 74 will wake up from the sleep mode. The microprocessor 74 may then check the state of input pin 4 (150)—which is coupled to the switch 70 through connector J1 (164). If input pin 4 (150) is high, then the push button 14 is not presently depressed or closed by the user to engage the switch 70. The microprocessor 74 may then perform other housekeeping tasks and re-enter sleep mode after turning off the boost section 189 by setting output pin 3 (154) high. This process may repeat periodically (e.g., every 1 second) so the microprocessor 74 can check the state of the switch 70 approximately every 1 second from a sleep state. Also, when the button 14 is pressed closing switch 70, the input pin 4 of NAND gate U2:B (183) is set low and the output of NAND gate U2:B (183) is set high, which actuates the oscillator 190, which further activates the boost circuit 189. This will, in turn, awake the microprocessor 74 from a sleep state.

In another embodiment, when the microprocessor 74 detects a depression of the push button 14 to temporarily close the switch 70, the microprocessor 74 sets the motors 30, 36 to operate in a high speed mode. A high speed mode may be created by setting output pin 13 (156) high, which connects the negative terminals of the motors 30, 36 to ground through the transistor Q1:B (175). In the high speed operation, the battery voltage VBAT (165) (i.e., 2.4 volts) is applied across the terminals of the motors 30, 36. The microprocessor 74 may apply the voltage VBAT (165)

across the terminals of the motors 30, 36 for a limited period of time, for example, three minutes.

In a further embodiment, if the microprocessor 74 detects a second depression of the button 14 indicated by a temporary closure of the switch 70 while the motors 30, 36 are driven in a high speed mode, the microprocessor 74 may disable output pin 13 (156) and enable output pin 12 (155). Output pin 12 (155) drives the base of transistor Q1:A (174), which provides a reduced voltage across the terminals of the motors through resistor R14 (193), which may be, for example, 0.68 ohms. In this manner, the motors 30, 36 will then operate in a low speed mode. If, during low speed operations, the microprocessor 74 detects another push button 14 depression indicated by a temporary closure of switch 70, the microprocessor 74 may disable both output pin 12 (155) and output pin 13 (156), thereby disabling both motors 30, 36 from running and deactivating the oral hygiene device 2.

An additional feature may be provided in the circuit of FIGS. 14A and 14B to monitor and charge the battery 40. Microprocessor output pin 16 (158) controls the base of transistor Q3 (194). When the oral hygiene device 2 is placed in a base charging unit 100 (see FIG. 15) transferring voltage through charging coil/magnet 44 and connector J4 (167), the signal VCHG1 (195) from diode CR1 (168) is set high, which is detected by input pin 15 (152) of the microprocessor 74. Further, the microprocessor 74 can track the battery voltage level through input pin 10 (151), which is coupled to the VBAT (165) battery voltage level. Accordingly, when the microprocessor 74 detects that the charging coil/magnet 44 has a voltage from the base charging unit 100, the microprocessor 74 can then determine whether to activate transistor Q3 (193), by setting low the output pin 16 (158) of the microprocessor 74, so that a charging voltage from the charging coil/magnet 44 is applied to the terminals of the rechargeable batteries 40. When output pin 16 (158) is set low, transistor Q3 (193) is activated and the battery 40 charges; when output pin 16 (158) is set high, transistor Q3 (193) is deactivated and the voltage from the charging coil/magnet 44 is no longer applied to the terminals of the battery 40.

In one embodiment, if the microprocessor 74 senses that the battery voltage signal VBAT (165) is too low (e.g., below 2.0 volts) then the microprocessor 74 can disable any motor operations or ignore any depressions of the push button 14 by the user closing the switch 70 until the oral hygiene device 2 has been placed in the base charging unit 100 and the battery voltage is restored to an acceptable level.

In a further embodiment, one or more nickel metal hydride rechargeable batteries 40 may be used in the oral hygiene device 2. In this instance, the microprocessor 74, using one or more persistent timers may keep track, for example, of the amount of time the motors 30, 36 are actuated, the amount of time the battery 40 charges, and the amount of time that the oral hygiene device 2 is both off and not in the base charging unit 100. In this manner, the microprocessor 74 can charge the nickel metal hydride battery 40 using timer information as well as the battery voltage signal VBAT (165) and thereby prevent overcharging of the nickel metal hydride battery 40. If a Nicad or other rechargeable battery 40 is used, the microprocessor 74 may be programmed to charge the battery 40 using, for example, a drip charge method.

While embodiments of the present invention are shown and described in terms of NPN/PNP transistors and field effect transistors, it is understood that other switching devices may be used, for example, n-channel or p-channel CMOS transistors, MOS-FETs, FETs, JFETS, or other similar switching elements or devices. The particular type of switching element used is a matter of choice depending on the particular application of the circuit, and may be based on many factors, for example, power consumption limits, response time, noise immunity, and fabrication considerations.

Further, embodiments of the present invention are described in terms of a circuit which utilizes logic levels of low (e.g., 0 volts) and high (e.g., +5 volts). It is understood that embodiments of the present invention can be utilized in circuits wherein the logic levels are different, for example, in a circuit which utilizes logic levels of 0 volts (logic low) and +3 volts (logic high), or otherwise.

Motion of Shaft and Hygiene Attachments

Typically, due to space limitations, the primary motor 30 will be larger than the secondary motor 36. Given the structure of the oral hygiene device 2, as shown in FIG. 7, it is contemplated that the secondary motor 36 will generate vibrational energy with a lower frequency and higher amplitude than the primary motor 30, which would generate vibrational energy with a relatively higher frequency and lower amplitude than the secondary motor 36. However, the oral hygiene device 2 could be constructed with the primary motor 30 of a lower frequency and higher amplitude than the secondary motor 36, a higher frequency and higher amplitude than the secondary motor 36, a lower frequency and lower amplitude than the secondary motor 36, or both motors 30, 36 could have identical vibrational frequencies and amplitudes as desired. The selection of the vibrational frequency and the amplitude may be made to maximize the effectiveness of the cleaning motion of the tip 12 and the oral hygiene attachment 250. Depending upon the type of oral hygiene attachment 250, achieving a desired level of effectiveness might require different combinations of motor placement, for example, placing both the primary motor 30 and the secondary motor 36 in the handle housing 3, placing both motors 30, 36 in the shaft 8, placing the primary motor 30 in the shaft 8 and the secondary motor 36 in an oral hygiene attachment 250, or placing the primary attachment 250.

Figure 29:
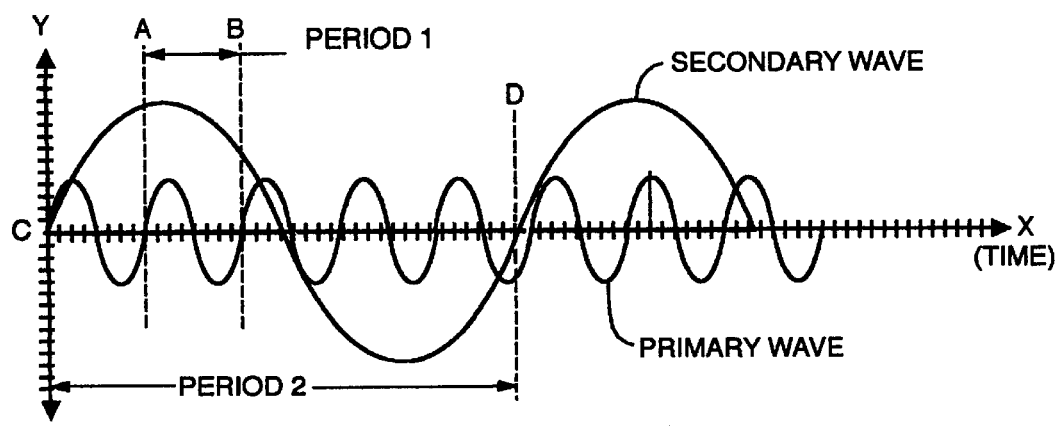
FIG. 29 illustrates the difference in amplitude and frequency of energy imparted by the dual motors in accordance with one embodiment of the present invention.

FIG. 29 shows an exemplary two dimensional representation of vibrational waves created by both the primary motor 30 and the secondary motor 36 in the present invention. One wavelength of the vibration imparted by the primary motor 30 (indicated as "primary wave") starts at point A and ends at point B and one wavelength of the vibration imparted by the secondary motor 36 (indicated as "secondary wave") starts at point C and ends at point D. In FIG. 29, the x-axis represents time and the y-axis distance.

FIGS. 30–33 illustrate the vibrational periods, frequencies, and amplitudes of both motors 30, 36 during operation. The period ("T") of a vibrational wave is the time required for the wave to move a distance equal to one wavelength. As shown FIG. 29, the time it takes a secondary wave to move a distance equal to one secondary wavelength is much greater than the time it takes a primary wave to move a distance equal to one primary wavelength. Therefore, the secondary wave period ("period 2") is much greater than the primary wave period ("period 1").

The frequency ("V") is equal to the number of periods created by a vibration in one second and is equal to 1/T, the inverse of the period. Correspondingly, the primary motor 30 in this embodiment has a higher frequency than the vibrational wave of the secondary motor 36, which has a much longer period.

The amplitude ("A") corresponds to the offset distance between a center axis and the farthest movement of the motor from the center axis. In FIG. 29, the amplitudes of the waves created by the vibration of the motors 30, 36 are shown by the offset of the waveforms from the X-axis in the Y-axis directions. The amplitude of the primary wave created by the primary motor 30 is smaller than the amplitude of the secondary wave created by the secondary motor 36. Thus, a gross or large-scale vibrational movement of the tip 12 is caused by the secondary motor 30 and the small scale, pseudo-random motion of the tip 12 is caused by the vibration of the primary motor 36.

Various movements of the tip 12 that may be created by the secondary motor 36 in the oral hygiene device 2 are shown in FIGS. 35–39. In FIG. 35, the tip 12 (shown with a toothbrush 200 attachment) moves in response to a linear vibration, primarily in one dimension from front to back. In FIG. 36, a linear vibratory motion is created primarily in one dimension side-to-side. This second motion may be created by the motor disclosed in U.S. Pat. No. 5,378,153, which is hereby incorporated herein by reference in its entirety.

FIG. 37 illustrates an oscillatory, rotational motion of the tip 12 that oscillates about an axis A along the length of the shaft 8 of the oral hygiene device 2. The toothbrush 200 first turns clockwise and then counterclockwise. This type of motion may be created by a motor such as those described in U.S. Pat. Nos. 5,613,259 and 5,341,534, which are hereby incorporated herein by reference in their entirety.

FIG. 38 shows an orbiting motion of the tip 12 about an axis A along the length of the shaft 8 of the oral hygiene device 2. This motion is may be achieved by the use of an eccentric mass motor, for example, a Jinglong Co. (China) model OTL-6CL or equivalent. The orbital motion about the axis A may be continuous in one direction, either clockwise or counterclockwise, if the motor shaft rotates continuously in one direction, or the orbital motion may be oscillatory, first moving clockwise and then counterclockwise along the orbital path, if the motor shaft rotates in an oscillatory pattern.

FIG. 39 shows an axial, reciprocating motion along the axis A of the shaft 8. This type of motion can be created by the vibrational motor as disclosed in U.S. Pat. No. 5,226,206, which is hereby incorporated by reference in its entirety.

FIG. 24 shows a schematic of the motor frame 32 and the surrounding structure that affects the motion of the motor frame 32, and thus the various oral hygiene attachments 250 to the tip 12. The base end 31 of the motor frame 32 is attached to the motor mount 50. The mid portion of the housing is constrained about the circumferential pivot point 25 at the O-ring 24. The primary motor 30 is positioned in the motor frame 32 near its base end 31, with the eccentric mass 60 positioned as far toward the base end 31 as possible. A secondary motor 36 is positioned within the shaft 8 on the opposite end of the motor frame 32, with its eccentric mass 64 positioned as far toward the tip 12 as possible. The motor mount 50 is held in place by its interface with the motor frame 32 and the lower handle housing 4 (as shown in FIG. 5). The circumferential pivot point 25 is likewise held in place by its interface with the shaft 8 of the motor frame 32 and the upper handle housing 6.

The point of intersection between the O-ring 24, the annular backplate 28, and the annular sealing shoulder 7 may act as a circumferential pivot point 25 (i.e., pivoting may occur about more than one pivot axis) about which the vibration of the motor frame 32 is translated into vibration of the shaft 8, and thus the tip 12 and any oral hygiene attachment 250 attached thereto. In some embodiments, the O-ring 24 may serve to isolate the vibrations of the secondary motor 36 from the handle housing 3, of the oral hygiene device 2. In one embodiment, the primary motor 30 and the secondary motor 36 are positioned at opposing ends of the motor frame 32 structure, as shown in FIG. 5. The motors 30, 36 may further be oriented so that the eccentric masses 60, 64 of each motor 30, 36 are positioned away from the pivot point 25 to generate a greater amount of vibration about the tip 12 of the shaft 8. The O-ring 24 may also act as a spring that generates alternate vibratory frequencies and patterns in the oral hygiene device 2. The variations in the vibrational energy are caused by a "rebound" motion of the shaft 8 as it presses against the O-ring 24 and the interior of the upper handle housing 6 adjacent the O-ring 24. The compression and decompression of the O-ring 24 interacts with the vibration patterns of the motors 30, 36 and causes additionally complex vibration patterns within the oral hygiene device 2.

Figure 30:
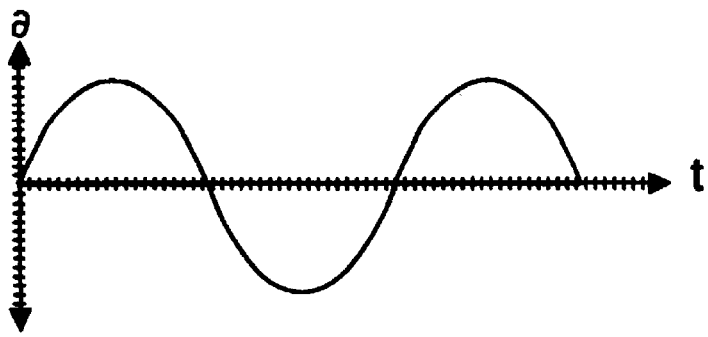
FIG. 30 illustrates the waveform of the energy imparted to the oral hygiene device by a first motor in accordance with one embodiment of the present invention.
Figure 31:
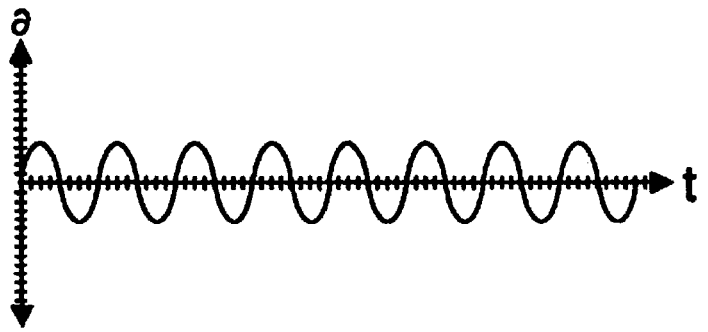
FIG. 31 illustrates the waveform of the energy imparted to the oral hygiene device by a second motor in accordance with one embodiment of the present invention.
Figure 32:
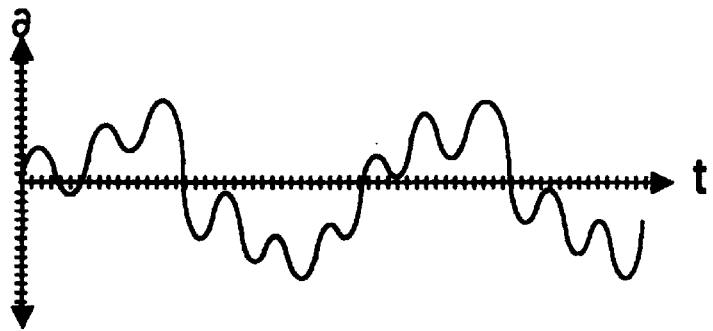
FIG. 32 illustrates the waveform of the effect on the energy imparted to the oral hygiene device by the first motor and the second motor by a mounting structure in accordance with one embodiment of the present invention.
Figure 33:
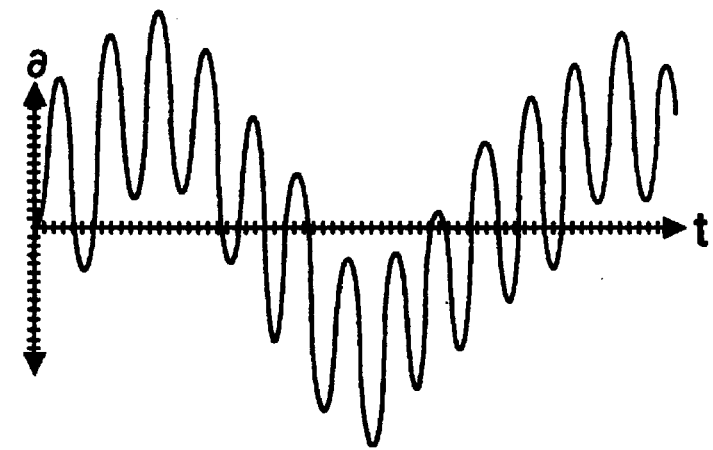
FIG. 33 illustrates sum of the waveforms of FIGS. 30–32 in accordance with one embodiment of the present invention.

Ultimately, the motion of the tip 12 of the oral hygiene device 2 will be the sum of several vibrations and effects including the vibration generated by the primary motor 30, the vibration generated by the secondary motor 36, spring and dampening effects of the O-ring 24, and focusing and dampening effects of the motor mount 50. FIG. 30 represents in two dimensions an isolation of the vibrational motion generated by the secondary motor 36. FIG. 31 represents in two dimensions an isolation of the vibrational motor generated by the primary motor 30. FIG. 32 represents in two dimensions an isolation of the vibrational motion generated from the O-ring 24 spring effect. FIG. 33 is a representation in two dimensions of a sum of the wave forms in FIGS. 30–32. The end result of the combined vibrations and effects is a tip 12 that has a combination of motions. The combination of vibrational motions with varying amplitudes, frequencies, and periods enhances the overall effectiveness of the oral hygiene device 2.

When the secondary motor 36 is positioned within the shaft 8 of the motor frame 32 and activated, the tendency of the secondary motor 36 is to create a vibrational force causing the motor-frame 32 to revolve or orbit about the O-ring pivot point 25. The force create by the secondary motor in the shaft 8 creates a greater moment the closer the eccentric mass 64 is to the tip 12 of the shaft 8. In one embodiment, the motor mount 50 is designed to influence the motion of the tip 12 in a generally elliptical pattern, as opposed to a circle, so that the tip 12 ultimately moves in and out a greater distance than side to side in an ellipse having its major axis extending parallel with the plane of the user's teeth or other oral surface for cleaning, for example, the tongue. To encourage this motion, the motor mount 50 may be formed with parallel lateral edges 55*a* and 55*b* and a curved front edge 56*a* and a back edge 56*b*, as shown in FIGS. 8–12.

As used herein, the directions of movement of any components of the oral hygiene device 2, e.g., the motor mount 50, the shaft 8, and ultimately an oral hygiene attachment 250, are indicated with respect to the interface between the oral hygiene attachment 250 and a user's teeth. Therefore, "front" indicates the side of the oral hygiene device 2, and its components, parallel to the side of an oral hygiene attachment 250 that is designed to contact the user's teeth, e.g., the side with bristles 202 (see FIG. 20), a flosser tip 212*a* (see FIG. 21) or a prophy polishing cup 222 (see FIG.

22). "Back" indicates the side opposite the front side. "Front to back" or "in and out" therefore describe movement of the shaft 8 or oral hygiene attachment 250 toward and away from the surface of the user's teeth. "Lateral," "side-to-side," and "left" and "right" therefore indicate the sides adjacent to the front side as viewed from the front side.

In this embodiment, the curved front edge 56a and back edge 56b of motor mount 50 are, by design, less compressible and thus limit the motion of the shaft 8 and oral hygiene attachments 250 primarily caused by the secondary motor 36 into and out of the plane of a user's teeth as the oral hygiene device 2 is used. By forming the front edge 56a and back edge 56b with a stiffer resilience, those portions of the motor mount 50 deform less under the force of the secondary motor 36. In contrast, the parallel lateral edges 55a and 55b may be designed to provide less dampening than the front edge 56a and back edge 56b, thus permitting the force generated by the secondary motor 36 to move the shaft 8 side-to-side (and in-and-out to a limited extent). The stiffness of various areas of the motor mount 50 may be affected by its material properties, for example, the type of material used, the thickness of the material, and the form of the material, as well as structural restrictions formed in the lower handle housing 4. This movement of the shaft 8 imparted by the secondary motor 36 and influenced by the motor mount 50 defines a roughly elliptical path having a major axis extending substantially parallel with the plane of the user's teeth.

It should be understood that the motor mount 50 shown herein in FIGS. 8–12 is sized and shaped to promote a side-to-side motion of the tip 12 of the shaft 8. However, a motor mount 50 of different size or shape may be used to impart a different fundamental motion on the shaft 8 of the oral hygiene device 2, for example, a circular motion, an elliptical motion with a major axis in a plane normal to or at another angle to the users teeth, a planar side-to-side translation pattern, a planar up-and-down pattern, or a planar in-and-out translation pattern.

If the motor mount 50 is designed to apply a generally equal force to all sides of the motor frame 32 as indicated in FIG. 25A (the "x" in each of the exemplary sections of the motor mount 50 indicates the equivalence of the level of compressibility of each section), the movement of the base end 31 of the motor frame 32 will be generally circular as shown in FIG. 25B. Likewise, if the circumferential pivot point 25 is designed to apply a generally equal force to all sides of the shaft 8 of the motor frame 32, the movement of the tip 12 of the shaft 8 will also be generally circular as shown in FIG. 25C. The motions depicted in FIGS. 25B, 25C, 26B, 26C, 27B, 27C, 28A, and 28B are exaggerated for explanatory purposes.

Assuming constant rotations per minute (RPM), locations, and eccentric masses 60, 62 for the primary motor 30 and the secondary motor 36, the motion of the tip 12 can be adjusted by changing either the forces applied to the base end 31 of the motor frame 32, the circumferential pivot point 25, or both. For example, the lateral motion of the base end 31 and the tip 12 can be reduced by stiffening the material of the motor mount 50 adjacent to the lateral sides of the motor frame 32 relative to the material of the motor mount 50 adjacent to the front and back sides of the motor frame 32, as shown in FIG. 26A by the indication of "+" signs for areas of greater stiffness and "−" signs for areas of lesser rigidity (or by otherwise restricting the movement of the motor frame 32 in the side-to-side direction). The material of the motor mount 50 may be of varying consistency or varying substances in order to provide the variable elasticity desired. Alternatively, or additionally, apertures 48 or recesses may be formed in the motor mount 50 to remove some of the material forming the motor mount 50 and increasing its deformability in resistance to the forces imparted by the primary motor 30 and the secondary motor 36. As shown in FIGS. 26B and 26C, this configuration of the motor mount 50 would cause the motor frame 32 to follow a generally elliptical orbit with a major axis extending vertically relative to the circular paths shown in FIGS. 25B and 25C. (The paths described herein may not precisely be elliptical as technically defined, but may be any of a variety of oblong closed loops).

Additionally, the forward and backward motion of the base end 31 and the tip 12 can be reduced by stiffening the material of the motor mount 50 adjacent to the front and back of the motor frame 32 relative to the material of the motor mount 50 adjacent to the lateral sides of the motor frame 32, as shown in FIG. 27A by the indication of "+" signs for areas of greater stiffness and "−" signs for areas of lesser rigidity (or by otherwise restricting the movement of the motor housing in the up and down direction). As shown in FIGS. 27B and 27C, this configuration of the motor mount 50 would cause the motor frame 32 to follow a generally elliptical orbit with a major axis extending laterally relative to the circular paths shown in FIGS. 25B and 25C.

Further modification of the motion of the base end 31 or tip 12 may be made by further restricting the ability of the motor frame 32 to move, in any number of manners. For example, as shown in FIG. 5, the upper handle housing 6 engages the shaft 8 of the motor frame 32 at the annular shoulder 10 above the O-ring 24 (circumferential pivot point 25). A gap is formed between the shaft 8 of the motor frame 32 and the annular shoulder 10 of the upper handle housing 6 above the circumferential pivot point 25, toward the front side of the oral hygiene device 2. Toward the back side of the oral hygiene device 2, the upper handle housing 6 extends further upward and the back side of the shaft 8 sits firmly against the upper housing handle 6. This configuration would restrain the motion of the base end 31 and the shaft 8 from movement in an upward direction (negating any flexure of the motor frame 32 between the pivot point 25 and the motor mount 50 attachment point) and limit the ability of the shaft to move toward the rear of the oral hygiene device 2, but would not restrain the shaft 8 from moving toward the front of the oral hygiene device 2. The resulting pattern of the movement of the base end 31 of the motor frame 32 and the tip 12 would be similar to the patterns shown in FIGS. 28A and 28B, respectively.

The pattern of motion of the tip 12 of the shaft 8 can be further modified by other adjustments to the physical surroundings of the motor frame 32. For example, the motor mount 50 could be designed to have differing compression characteristics on different sides (as opposed to symmetrical compression characteristics as described above). Further, hard physical restraints, for example, formed in the design of the lower handle housing 4 or upper handle housing 6, could be used to modify the motion as desired.

In addition to affecting the movement of the shaft in response to the vibrations of the secondary motor 36, the motor mount 50 also controls and limits the movement imparted by the primary motor 30 to the motor frame 32 within the handle housing 3 of the oral hygiene device 2. When the primary motor 30 is actuated, the eccentric mass 60 urges the base end 30 of the motor frame 32 to move in an orbital path. However, because the motor mount 50 is tightly fitted to the motor frame 32 adjacent to the position of the eccentric mass 60 and also tightly fitted against the interior of the handle housing 3, the actual movement of the base end 31 of the motor frame 32 due to the effects of the primary motor 30 is comparatively minimal to that of the shaft 8. The motion that does result is similarly affected by the characteristics of the motor mount 50 in the same manner as described above with respect to the effects on motion caused by the secondary motor 36. Further, because of the higher frequency and lower amplitude of the vibrations of the primary motor 30, the resulting motion imparted by the primary motor 30 on the motor frame 32 is of a lesser magnitude than that imparted by the secondary motor 36. Because the motor frame 32 is connected with the shaft 8, the vibrations of the primary motor are translated to the shaft tip 12 resulting in randomizing effects on the patterns of movement observed in the shaft 8 and oral hygiene attachments 250. For example, in one embodiment, the movement of the shaft was observed to be an eccentric, substantially elliptical path, i.e., the elliptical path of the shaft 8 was not symmetric to the front and back and lateral sides of the oral hygiene device 2, but instead the major axis of the elliptical path was diagonal between the back left and front right of the oral hygiene device 2.

The force of the primary motor 30 translates through the motor frame 32 and across the pivot point 25 into motion of the tip 12 of the shaft 8 in a similar orbital path 180° out of phase. In the embodiment disclosed in FIGS. 4 and 5, the eccentric mass 60 of the primary motor 30 is oriented toward the base end 31 of the motor frame 32 and the eccentric mass 64 of the secondary motor 36 is oriented toward the tip 12. The Jinlong and Mabuchi motors previously described were chosen such that the shaft of the secondary motor 36 rotates clockwise and the shaft of the primary motor 30 rotates counterclockwise. In this manner, there are period wherein the rotations of the eccentric masses 60, 64 are exactly in phase and create greater arcs of movement in the tip 12. Similarly there are times when the rotations of the eccentric masses 60, 64 are partially or completely out of phase causing some cancellation of the vibratory energy and resulting in a dampening of the orbital radius of the tip 12. Alternately, the rotation of both the primary motor 30 and the secondary motor 36 may be clockwise or counterclockwise. With the eccentric masses 60, 64 facing opposite directions, there will primarily be at least a partial cancellation of the vibrations imparted by the motors, however, there will occasions of constructive movement imparted to the shaft 8 as well.

In alternate embodiments, the primary motor 30 and the secondary motor 36 may be mounted such that the eccentric masses 60, 64 are aligned in the same direction, either toward the tip 12 or toward the base end 31, or the eccentric masses 60, 64 may face each other in the middle of the motor frame 32. Alternatively, or in addition, the rotation of the motors may be in the same or opposite directions. Each combination will result in a different, random effect on the movement of the oral hygiene attachment 250.

The movement of a tip of the oral hygiene attachment 250 actually attached to the oral hygiene device 2, for example, the tip of each bristle 202 on the toothbrush 200, or the tip of the single element flosser 212a, is defined by the structural relationship of the oral hygiene attachment 250 tip to the tip 12 of the shaft 8, and the physical characteristics of the oral hygiene attachment 250 tip. For example, with a toothbrush 200 attached to the shaft 8, each individual bristle 202 extends substantially normal to the front of the shaft 8. If the movement of the tip 12 of the shaft 8 is designed to be an elongated ellipse with a major axis extending parallel to the surface of the teeth, the tip of an individual bristle 202 on the toothbrush 200 will move substantially in a flat elliptical motion perpendicular to the plane of the surface of the teeth. In effect, the bristle tip will move side-to-side a great deal more than it will move forward and backward (i.e., toward and away from the teeth). If the oral hygiene device 2 is held generally horizontally, as is usually the case, the major bristle motion will be up and down with respect to the adjacent surface of the user's teeth, with a minor motion toward and away from the teeth to promote cleaning of the crevices between teeth and along the gum line.

In addition to the movement caused by the secondary motor 36, the actuation of the primary motor 30, positioned in the motor frame 32 in the upper handle housing 6 imparts an additional movement characteristic to the tip 12 of the shaft 8 as well as the tip of the oral hygiene attachment 250 attached to the shaft 8. The characteristics of the primary motor 36, for example, speed (frequency of rotation), eccentricity (force attributable to the eccentric mass 60), and position in the oral hygiene device 2, affects the ultimate motion imparted to the tip 12 of the shaft 8 and the tip of the oral hygiene attachment 250 attached to the shaft 8. This additional motion, combined with the motion caused by the secondary motor 36, also results in a randomized movement of the tip 12 of the shaft 8, and the tip of the oral hygiene attachment 250 attached to the shaft tip 12. In one embodiment, the characteristics of the primary motor 30 may be chosen to excite the natural frequency of the bristles 202 of a brush head 200 attachment. By exciting the natural frequency of the bristles 202 with the vibration of the primary motor 30, a maximum number of brush strokes per minute by each bristle 202 may be achieved for optimum cleaning efficacy by the brush head 202. In one embodiment, it was observed that the natural frequency of the bristles was approximately 48,000 brush strokes per minute (bspm). In one observation, when both the primary motor 30 and secondary motor 36 were energized, the bristles were excited to their natural frequency of 48,000 bspm. In varying observations, it was observed that the brush strokes per minute achieved using various combinations of the motors, for example, the primary motor 30 individually, the secondary motor 36 individually, or both the primary motor 30 and secondary motor 36 together were between 15,000 and 50,000 bspm.

Figure 18:
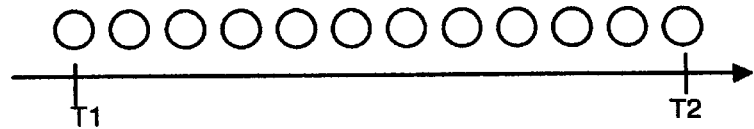
FIG. 18 illustrates front view of a bristle showing an example of bristle motion.
Figure 19:
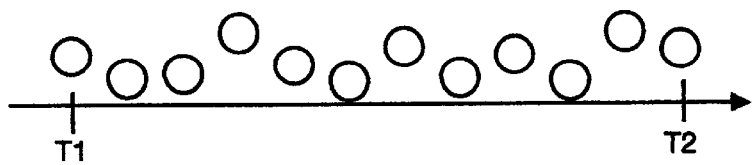
FIG. 19 illustrates front view of a bristle showing an example of bristle motion in accordance with one embodiment of the present invention.

It has been particularly found that the primary motor 30 imparts a second frequency or set of frequencies of vibration to the shaft 8 during each period of gross movement of the shaft 8 caused by the secondary motor 36. This effect is generally illustrated in FIGS. 18 and 19. FIG. 18 shows the motion of a tip of a bristle between time 1 and time 2, where only the secondary motor 36 is actuated. The pattern of motion is curvilinear, and is part of the elliptical motion pattern described herein. The bristle tip will return to its position at time 1 as the shaft 8 completes its revolution about the pivot point 25. A brush stroke is defined as lateral motion of the tip of a bristle in one direction. Therefore, an entire elliptical orbit of a bristle tip results in two brush strokes as it move from the starting point to the distal point of the major axis and back to the starting point.

FIG. 19 shows a representative motion of the tip of a bristle during the same time period when both the primary motor 30 and secondary motor 36 are actuated. FIG. 19 shows the divergence of the position of the tip of a bristle, relative to time, from the expected baseline motion created by the primary motor 30 alone. It should be understood that FIGS. 18 and 19 illustrate a single example of a movement of a single bristle tip (or single flosser tip), and the examples of FIGS. 18 and 19 are not intended to limit or characterize all possible bristle movements, either individually or in groups, or the movement of any of the other oral hygiene attachment 250 tips, that may be achieved through the use of various embodiments of the present invention.

FIGS. 18 and 19 do show that the use of two motors can impart different vibrations to the tip 12 of the shaft 8, and thus the tip of the oral hygiene attachment 250, to cause a substantially random movement. Such a random movement allows the oral hygiene device 2 to provide an effective cleaning or polishing effect on a user's teeth. This substantially random movement may not be purely random, but instead may be a complex movement having multiple additive frequency components, creating a pseudo-random state, which may or may not repeat in a periodic or non-periodic manner.

In one exemplary embodiment of the oral hygiene device 2 employing the Mabuchi motor described above for the primary motor 30 and the Jinlong motor described above for the secondary motor 36, the motion imparted to the shaft 8, an attached brush head 200, and the bristles 202 thereof was studied. FIGS. 40A, 40B, 41A, 41B, 42A, and 42B disclose measurements and graphical plots of particular cycles of movement observed for a single full cycle of movement of the shaft 8 without an oral hygiene attachment 250 affixed (FIGS. 40A and 40B), a brush head 200 attached to the shaft 8 (FIGS. 41A and 41B), and the movement of the bristles 202 on the brush head 200 (FIGS. 42A and 42B). Each of the tables of measurements taken and related plots derived only depict one sample cycle. Any measurements taken and related plots derived for a cycle observed at a different time would be different than those depicted in FIGS. 40A, 40B, 41A, 41B, 42A, and 42B because of the substantially random effect on the movement of the oral hygiene device 2 caused by the interaction of the primary motor 30 and the secondary motor 36. Further, the measurements and related plots shown in FIGS. 40A, 40B, 41A, 41B, 42A, and 42B are not of the same cycle of movement. The measurements of each component (i.e., shaft 8, brush head 200, and bristles 202) were taken at different times and are of different movement cycles.

Figures 40A, 40B:
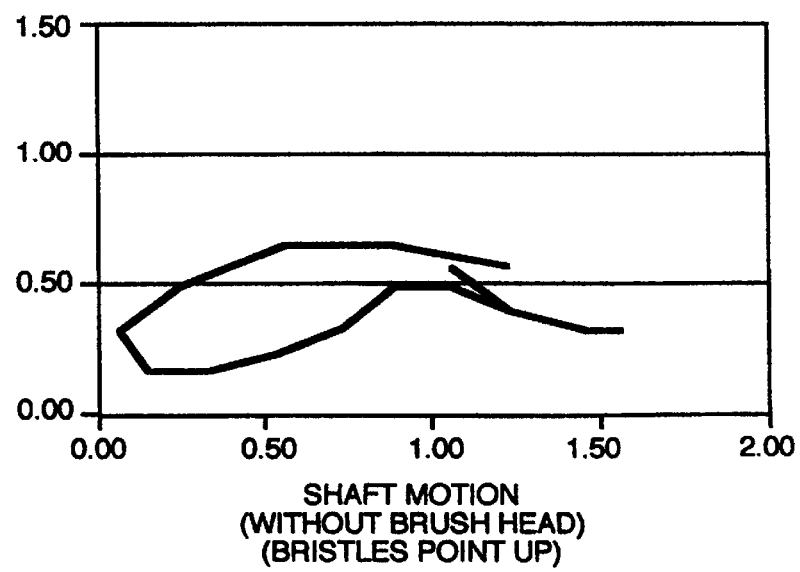
FIGS. 40A–40B are measurements and a plot of the movement of the tip of the shaft of a dual motor toothbrush in accordance with one embodiment of the present invention.
Figures 41A, 41B:
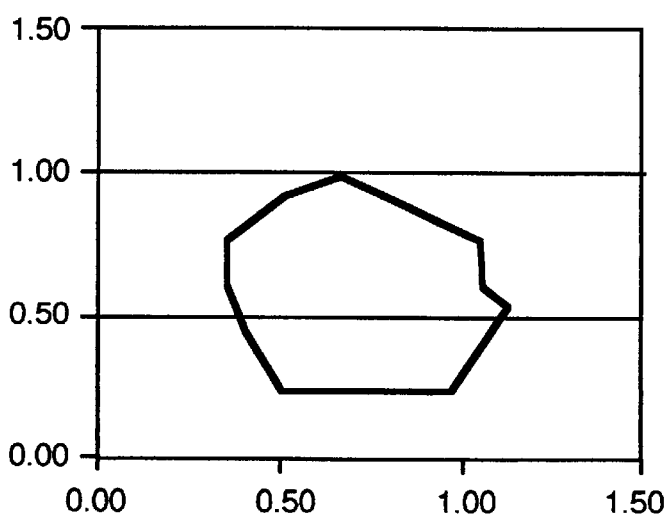
FIGS. 41A–41B are measurements and a plot of the movement of a brush head of a dual motor toothbrush in accordance with one embodiment of the present invention.
Figures 42A, 42B:
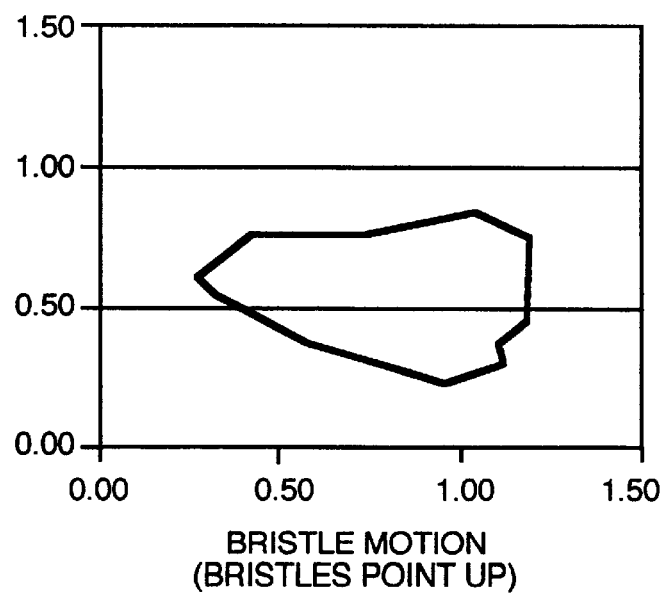
FIGS. 42A–42B are measurements and a plot of the movement of the bristles on brush head of a dual motor toothbrush in accordance with one embodiment of the present invention.

The plots of FIGS. 40B, 41B, and 42B are, however, instructive of the types of movements expected from the oral hygiene device 2. In FIG. 40B the motion of the shaft 8 as viewed from the tip 12, under influence of both the primary motor 30 and the secondary motor 36, without a brush head 200 or other oral hygiene attachment 250, is depicted. The movement is most closely elliptical, although with oblong variations in the path. This is due to the interplay between the vibration effects of the primary motor 30 and the secondary motor 36, which combine to produce the random movement pattern of the shaft 8 as measured. During one portion of the period, the shaft 8 actually retraces part of the path it previously traveled. As indicated, if a brush head 200 were attached, the bristles 202 would point upward with respect to the plot. Therefore, it is apparent that the major motion of the shaft 8 is lateral along the tooth surface, but it also moves in-and-out to further force the bristles into tooth crevices and the gum line.

FIG. 41B shows the movement of a brush head 200 attached to the shaft 8 as viewed from the tip of the brush head 200. Again, the bristles 202 of the brush head 200 point upward with respect to the plot. The movement of the brush head 200 for the particular cycle measured is closer to fitting a circular shape than an elliptical shape and the length of the path traveled is shorter than that of the shaft 8 alone. This different movement may be the result of several factors. First, this movement is the random result of the combined vibrations of the primary motor 30 and the secondary motor 36 and may be different with different cycles. Second, because of the weight and structure added to the shaft 8 by the brush head 200, the motion maybe dampened by the addition of the brush head 200. Third, as previously discussed, the back of the upper handle housing 6 at the pivot point 25 may sit flush against the shaft 8 as shown in FIG. 5 without a gap as on the front side. Further, the flat, close interface between the sleeve 232 of the oral hygiene attachment 250 (in this case the brush head 200) (as shown in FIGS. 23B–23F) and the annular shoulder 10 of the upper handle housing 6 (see FIG. 5) may reduce the range of motion of the shaft 8 when the brush head 200 is attached. The brush head 200 does still move laterally along the surface of the teeth as well and toward and away from the teeth. In an alternative embodiment, if greater range of motion of the brush head 200 or other oral hygiene attachment 250 is desired, a gap may be provided between the bottom of the sleeve 232 and the annular shoulder 10 or a gap may be provided between the shaft 8 and the back of the upper handle housing 6 at the pivot point 25, similar to the relationship between the shaft 8 and the front of the upper handle housing 6 at the pivot point 25.

As indicated by the plot of FIG. 42B, even if the range of motion of the brush head 200 is limited by some constraint, the motion of the bristles 202 may not be similarly impacted. The motion of the bristles 202 for the cycle captured in the plot of FIG. 42B is substantially elongate and fits more closely with an elliptical pattern. The tips of the bristles 202 move a greater length laterally along the surface of the teeth than the brush head 200, as well as move in and out of the plane of the teeth. This greater range of movement may be attributable to the excitation of the natural frequency of the bristles 202 by the primary motor 30. Again, the plot of FIG. 42B shows the substantially random movement of the bristles 202 at any given time in the cycle, while still moving in a generally elliptical cycle from and macro viewpoint.

Figure 43A:
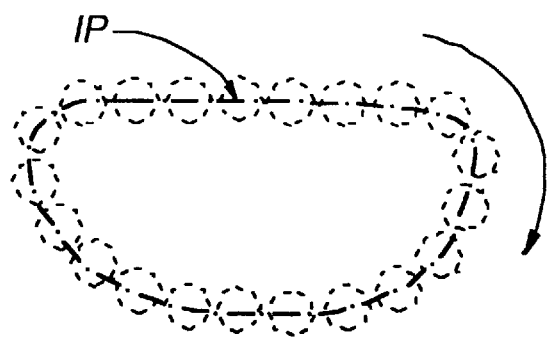
FIGS. 43A–43C are observations of exemplary patterns of periodic motion of the shaft of a dual motor toothbrush in accordance with one embodiment of the present invention
Figure 43B:
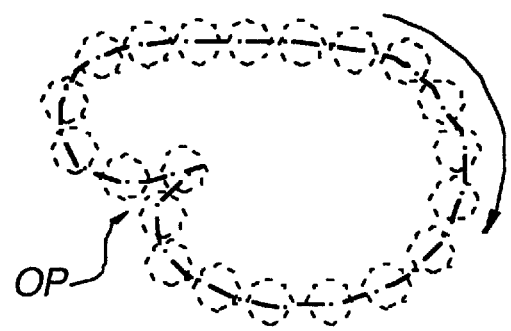
Figure 43C:
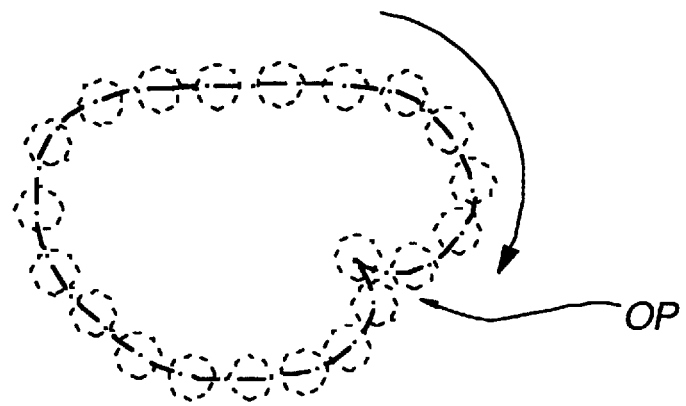

In one observation period, the macro motion of the shaft 8 was observed to repeat in a periodic manner. FIGS. 43A, 43B, and 43C are exemplary representations of the periodic motion of the tip 12 of the shaft 8 observed. The tip 12 generally followed the illustrated path of FIG. 43A for three cycles; then generally followed the path illustrated in FIG. 43B for three cycles; and finally generally followed the path illustrated in FIG. 43C for three cycles before reverting back to the path of FIG. 43A. The paths shown in these figures are approximations as the actual paths for each three-cycle period varied slightly and randomly due to the randomizing effects of the combination of the primary motor 30 and the secondary motor 36. At certain points during a cycle, the vibrations of the primary motor 30 and the secondary motor 36 may be in phase and cause a wider trajectory for a portion of the cycle, for example, as shown by the portion of the path marked IP. Contrarily, at certain points during a cycle, the vibrations of the primary motor 30 and the secondary motor 36 may be out of phase and may limit the trajectory for a portion of the cycle, or even cause a pause in the movement of the shaft 8, for example, as shown by the portion of the path marked OP.

All directional references used herein (e.g., front, back, upper, lower, upward, downward, in, out, lateral, left, right, leftward, rightward, top, bottom, above, below, vertical, horizontal, clockwise, and counterclockwise) are only used for identification purposes to aid the reader's understanding of the present invention, and are not intended to create limitations, particularly as to the position, orientation, or use of the invention.

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

While the invention has been particularly shown and described with reference to embodiments thereof, it will be understood by those skilled in the art that various other changes in the form and details may be made without departing from the spirit and scope of the invention.

What is claimed is:

1. A power oral hygiene device comprising:
   a main body having a handle portion and a head portion;
   an oral hygiene attachment connected to the head portion;
   a first vibratory means positioned in the handle portion operating at a first frequency and a first amplitude;
   a second vibratory means positioned in the head portion operating at a second frequency and a second amplitude; and
   a power means for providing energy to the first vibratory means and the second vibratory means; wherein
      the first frequency is greater than the second frequency;
      the second amplitude is greater than the first amplitude; and
      the first vibratory means and the second vibratory means operate in concert to impart an orbital motion with random or quasi-random variances to the head portion.

2. The device of claim 1, wherein the orbital motion further comprises a substantially elliptical orbital motion.

3. The device of claim 2, wherein the substantially elliptical orbital motion is eccentric.

4. The device of claim 2, wherein a major axis of the elliptical orbit is substantially parallel to a plane of an oral surface of a user when the oral hygiene attachment is operationally held against the oral surface and a minor axis of the elliptical orbit is substantially perpendicular to the plane of the surface of the oral surface when the oral hygiene attachment is operationally held against the oral surface.

5. The device of claim 1, wherein a first vibratory force imparted by the second vibratory means primarily contributes to the orbital motion and a second vibratory force imparted by the first vibratory means primarily contributes to the random or quasi-random variances.

6. The device of claim 1 further comprising a motor mount attached to the first vibratory means and tightly fitted against an interior surface of the handle portion, wherein
   the motor mount focuses vibratory energy generated by at least one of the first vibratory means and second vibratory means and imparts the vibratory energy to the head portion in at least one direction.

7. The device of claim 1 further comprising a pivot means between the handle portion and the head portion wherein a radius of the orbital motion of the head portion is constrained by the pivot means.

8. The device of claim 7, wherein the pivot means acts like a spring to impart additional complex motion to the head portion.

9. The device of claim 7, wherein the pivot means dampens the motion imparted to the head portion by the first vibratory means and the second vibratory means.

10. The device of claim 1, wherein a ratio of the first frequency to the second frequency is between 1.3 and 3.

11. A power toothbrush comprising:
    a main body having a handle portion and a head portion;
    the head portion further comprising a shaft portion and a brush head portion operably attached to the shaft portion;
    the brush head portion further having bristles;
    a first vibratory motor operating at a first frequency and a first amplitude positioned in the handle portion;
    a second vibratory motor operating at a second frequency and a second amplitude positioned in the head portion; and
    a power source for providing energy to the first motor and the second motor; wherein
       the first frequency is greater than the second frequency;
       the second amplitude is greater than the first amplitude; and
       the first vibratory motor and the second vibratory motor operate in combination to impart an orbital motion with random or quasi-random variances to the head portion.

12. The power toothbrush of claim 11, wherein at least one of the first motor and the second motor is an eccentric motor.

13. The power toothbrush of claim 11, wherein the first vibratory motor excites a natural frequency of the bristles.

14. The device of claim 11, wherein a proximal end of each of the bristles is fixedly attached to the brush head and a distal end of each of the bristles is free to move, and wherein the second vibratory motor causes an oscillatory motion in the distal ends of the bristles.

15. The device of claim 14, wherein combination of the first vibratory motor with the second vibratory motor excites distal ends of the bristles to randomly or quasi-randomly deviate from the oscillatory motion.

16. A power oral hygiene device comprising:
    a handle portion for grasping by a user;
    an oral hygiene portion attached to the handle portion at a pivot point; and
    at least one vibratory means; wherein
       the at least one vibratory means imparts an orbital motion to the oral hygiene portion, wherein a distal end of the oral hygiene portion orbits around an axis extending distally from the handle portion at the pivot point, and
       the at least one vibratory means comprises at least a first vibratory means and a second vibratory means, wherein the first vibratory means is positioned within the handle portion and the second vibratory means is positioned within the oral hygiene portion.

17. The device of claim 16, wherein the orbital motion is substantially elliptical.

18. The device of claim 17, wherein the substantially elliptical orbit is eccentric to the axis.

19. The device of claim 16, wherein the oral hygiene portion further comprises a brush head with a plurality of bristles and wherein the first vibratory means excites a natural frequency of the bristles.

20. The device of claim 19, wherein the plurality of bristles are grouped in at least one clump and wherein the first vibratory means excites a natural frequency of the at least one clump of bristles.

21. The device of claim 19, wherein the first vibratory means excites a natural frequency of the each of the bristles individually.

22. The device of claim 19, wherein the plurality of bristles are excited by at least one of the first vibratory means and the second vibratory means to impart between 15,000 and 50,000 brush strokes per minute.

23. The device of claim 19, wherein the plurality of bristles are excited by at least one of the first vibratory means and the second vibratory means to impart approximately 48,000 brush strokes per minute.

24. The device of claim 20, wherein a proximal end of each of the bristles is fixedly attached to the brush head and a distal end of each of the bristles is free to move, and wherein the second vibratory means causes an oscillatory motion in the distal ends of the bristles.

25. The device of claim 24, wherein combination of the first vibratory means with the second vibratory means excites distal ends of the bristles to randomly or quasi-randomly deviate from the oscillatory motion.

26. The device of claim 19, wherein a proximal end of each of the bristles is fixedly attached to the brush head and a distal end of each of the bristles is free to move, and wherein the second vibratory means causes an oscillatory motion in the distal ends of the bristles.

27. The device of claim 26, wherein combination of the first vibratory means with the second vibratory means excites distal ends of the bristles to randomly or quasi-randomly deviate from the oscillatory motion.

28. The device of claim 16, wherein the oral hygiene portion orbits in a substantially random pattern as a result of a combination of vibratory energy generated by the first vibratory means and vibratory energy generated by the second vibratory means.

29. A power oral hygiene device comprising:
a handle portion for grasping by a user;
an oral hygiene attachment;
at least one vibratory means; and
a frame that houses the at least one vibratory means, wherein the frame is positioned internal to and spaced apart from the handle portion and is connected to the oral hygiene attachment, wherein the frame imparts vibratory energy generated by the at least one vibratory means to the oral hygiene attachment; wherein
the at least one vibratory means comprises a first motor housed within a portion of the frame within the handle portion and a second motor housed within the shaft.

30. The device of claim 29 further comprising a motor mount positioned between the frame and the handle portion, wherein the motor mount focuses the vibratory energy generated by the at least one vibratory means and imparts the vibratory energy to the oral hygiene attachment in at least one direction.

31. The device of claim 29, wherein the frame further comprises a shaft protruding from within the handle portion and extending beyond the handle portion to engage the oral hygiene attachment; and
wherein an interface between the shaft and the handle portion comprises a pivot point about which the shaft of the frame orbits under influence of the vibratory energy.

32. The device of claim 31 further comprising an O-ring mounted to the handle portion at the pivot point wherein the O-ring imparts a spring effect on the orbit of the shaft.

* * * * *